(12) United States Patent
Levine

(10) Patent No.: US 7,448,752 B2
(45) Date of Patent: Nov. 11, 2008

(54) METHOD OF TREATING THE HUMAN EYE WITH A WAVEFRONT SENSOR-BASED OPHTHALMIC INSTRUMENT

(75) Inventor: Bruce Martin Levine, Arcadia, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 0 days.

(21) Appl. No.: 11/702,441

(22) Filed: Feb. 5, 2007

(65) Prior Publication Data

US 2007/0273830 A1  Nov. 29, 2007

Related U.S. Application Data

(63) Continuation of application No. 10/639,787, filed on Feb. 10, 2004, now abandoned, which is a continuation of application No. 09/874,903, filed on Jun. 5, 2001, now Pat. No. 6,609,794.

(51) Int. Cl.
*A61B 3/10* (2006.01)
(52) U.S. Cl. ........................ 351/205; 351/212; 351/221
(58) Field of Classification Search ................ 351/208, 351/205, 212, 221, 247, 216
See application file for complete search history.

(56) References Cited

U.S. PATENT DOCUMENTS 5,120,128 A * 6/1992 Ulich et al. ................. 356/121
5,684,545 A * 11/1997 Dou et al. ........................ 349/1
5,949,521 A * 9/1999 Williams et al. ............ 351/246

* cited by examiner

*Primary Examiner*—William C. Choi
*Assistant Examiner*—Jack Dinh
(74) *Attorney, Agent, or Firm*—Tarolli, Sundheim, Covell & Tummino LLP

(57) ABSTRACT

An improved method for treating the eye includes the step of providing an ophthalmic instrument including an integral wavefront sensor. The wavefront sensor measures phase aberrations in reflections directed thereto to characterize aberrations of the eye. The wavefront sensor may be operably coupled to a display device, which displays a graphical representation of the aberrations of the eye. Such graphical representation may include: two dimensional contour maps that graphically depict contribution of pre-specified terms (such as spherical aberration, astigmatism and coma) for the aberrations of the eye, coefficients corresponding to such pre-specified terms that characterize the aberrations of the eye, or predefined two-dimensional icons that provide a general graphical depiction of such pre-specified terms. Such graphical representations provide the practitioner with valuable information characterizing the high order optical errors of the eye (which is far beyond the diopter information typically provided by current ophthalmic instruments) for use in diagnosis and treatment of abnormalities and disease in the eye. In addition, the wavefront sensor may be part of an adaptive optical subsystem that compensates for the phase aberrations measured therein to provide phase-aligned images of the eye for capture by an image capture subsystem. Such images may be used by practitioner in diagnosis and treatment of abnormalities and disease in the eye.

8 Claims, 19 Drawing Sheets

Ideal Eye

Aberrated Eye

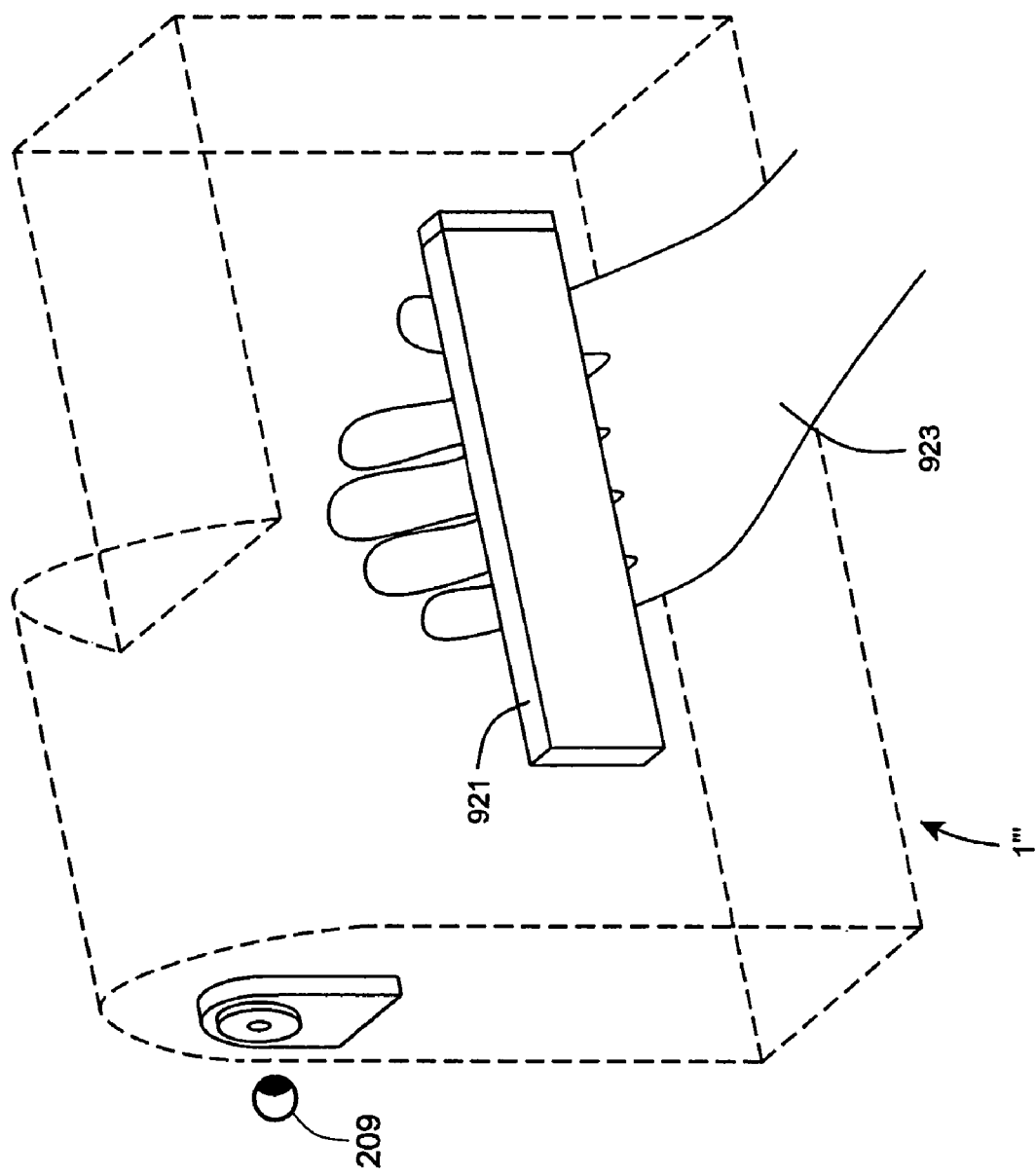

METHOD OF TREATING THE HUMAN EYE WITH A WAVEFRONT SENSOR-BASED OPHTHALMIC INSTRUMENT

CROSS-REFERENCE TO RELATED APPLICATIONS

The present application is a Continuation of U.S. application Ser. No. 10/639,787 filed Feb. 10, 2004; now abandoned which is a Continuation of U.S. application Ser. No. 09/874,903 filed Jun. 5, 2001, now U.S. Pat. No. 6,609,794; which is related to U.S. application Ser. No. 09/874,401 filed Jun. 5, 2001, now U.S. Pat. No. 6,582,079; U.S. application Ser. No. 09/874,403 filed Jun. 5, 2001; U.S. application Ser. No. 09/874,404 filed Jun. 5, 2001, now U.S. Pat. No. 6,572,230; each said application incorporated herein by reference in its entirety.

BACKGROUND OF THE INVENTION

1. Field of the Invention

The present invention relates to ophthalmic instruments that aid in detection and diagnosis of eye disease, pre-surgery preparation and computer-assisted eye surgery (such as laser refractive surgery), including ophthalmic imaging and/or topography instruments (such as fundus cameras, corneal imaging devices, retinal imaging devices, corneal topographers, and retinal topographers) in addition to ophthalmic examination instruments (such as autorefractors, slit lamps and other indirect opthalmoscopes).

2. Summary of the Related Art

The optical system of the human eye has provided man with the basic design specification for the camera. Light comes in through the cornea, pupil and lens at the front of the eye (as the lens of the camera lets light in). This light is then focused on the inside wall of the eye called the retina (as on the film in a camera). This image is detected by detectors that are distributed over the surface of the retina and sent to the brain by the optic nerve which connects the eye to the brain (as film captures the image focused thereon).

FIG. 1 shows a horizontal cross section of the human eye. The eye is nearly a sphere with an average diameter of approximately 20 mm. Three membranes—the cornea and sclera outer cover, the choroid and the retina—enclose the eye. The cornea 3 is a tough transparent tissue that covers the anterior surface of the eye. Continuous with the cornea 3, the sclera 5 is an opaque membrane that encloses the remainder of the eye. The choroid 7 lies directly below the sclera 5 and contains a network of blood vessels that serves as the major source of nutrition to the eye. At its anterior extreme, the choroid 7 includes a ciliary body 9 and an iris diaphragm 11. The pupil of the iris diaphragm 11 contracts and expands to control the amount of light that enters the eye. Crystalline lens 13 is made up of concentric layers of fibrous cells and is suspended by fibers 15 that attach to the ciliary body 9. The crystalline lens 13 changes shape to allow the eye to focus. More specifically, when the ciliary muscle in the ciliary body 9 relaxes, the ciliary processes pull on the suspensory fibers 15, which in turn pull on the lens capsule around its equator. This causes the entire lens 13 to flatten or to become less convex, enabling the lens 13 to focus light from objects at a far away distance. Likewise, when the ciliary muscle works or contracts, tension is released on the suspensory fibers 15, and subsequently on the lens capsule, causing both lens surfaces to become more convex again and the eye to be able to refocus at a near distance. This adjustment in lens shape, to focus at various distances, is referred to as "accommodation" or the "accommodative process" and is associated with a concurrent constriction of the pupil.

The innermost membrane of the eye is the retina 17, which lies on the inside of the entire posterior portion of the eye. When the eye is properly focused, light from an object outside the eye that is incident on the cornea 3 is imaged onto the retina 17. Vision is afforded by the distribution of receptors (e.g., rods and cones) over the surface of the retina 17. The receptors (e.g., cones) located in the central portion of the retina 17, called the fovea 19 (or macula), are highly sensitive to color and enable the human brain to resolve fine details in this area. Other receptors (e.g., rods) are distributed over a much larger area and provides the human brain with a general, overall picture of the field of view. The optic disc 21 (or the optic nerve head or papilla) is the entrance of blood vessels and optic nerves from the brain to the retina 17. The inner part of the posterior portion of the eye, including the optic disc 21, fovea 19 and retina 17 and the distributing blood vessels is called the ocular fundus 23.

A fundus camera is an optical instrument that enables a practitioner to view (and typically capture) an image of the ocular fundus 23 (or portions thereof) to aid the practitioner in the detection and diagnosis of disease in human eye. The fundus camera typically includes two different illumination sources—an observation source and a photographing source. The observation source, which is typically a halogen lamp or infra-red light source, is used during an observation mode of operation to view (observe) the ocular fundus 23 (or portions thereof) typically through a view finder. The photographing source, which is typically a xenon flash lamp, is used during a photographing mode of operation to photograph on film and/or capture on a CCD camera body, an image of the ocular fundus 23 (or portion thereof).

The fundus camera includes an optical subsystem that illuminates the ocular fundus 23 and collects the light reflected therefrom to produce an image of the ocular fundus 23. In the observation mode of operation, the observation source is activated (and the photographing source is de-activated). The optical subsystem illuminates the ocular fundus 23 with light produced from the observation source and collects the light reflected therefrom to produce an image of the ocular fundus 23 (or portions thereof) for view typically through a view finder. In the photographing mode of operation, the photographing source is activated (and the observation source is de-activated). The optical subsystem illuminates the ocular fundus 23 with light produced from the photographing source and collects the light reflected therefrom to produce an image of the ocular fundus 23 (or portions thereof) for capture on film or on the CCD camera body.

In addition, as is well known in the art, the optical subsystem of the fundus camera may include narrow band spectral filters for use in the photographing mode of operation to enable fluorescein angiography and/or indocyanine green angiography.

Examples of prior art fundus cameras are described in U.S. Pat. Nos. 4,810,084; 5,557,321; 5,557,349; 5,617,156; and 5,742,374; each herein incorporated by reference in its entirety.

Current fundus cameras suffer from the problem that the aberrations of the eye limit the resolution of the camera. More specifically, defocus such as myopia (near-sightedness) or hyperopia (far-sightedness) and astigmatism as well has many other higher order aberrations not only blur images formed on the retina (thus impairing vision), but also blur images taken of the retina of the human eye. A more detailed discussion of such aberrations is described by Williams et al.

in "Visual Benefit of Correcting Higher Order Aberrations of the Eye," Journal of Refractive Surgery, Vol. 16, September/October 2000, pg. S554-S559.

In U.S. Pat. Nos. 5,777,719, 5,949,521, and 6,095,651, Williams and Liang disclose a retinal imaging method and apparatus that produces a point source on a retina by a laser. The laser light reflected from the retina forms a distorted wavefront at the pupil, which is recreated in the plane of a deformable mirror and a Schack-Hartmann wavefront sensor. The Schack-Hartmann wavefront sensor includes an array of lenslets that produce a corresponding spot pattern on a CCD camera body in response to the distorted wavefronts. Phase aberrations in the distorted wavefront are determined by measuring spot motion on the CCD camera body. A computer, operably coupled to the Schack-Hartmann wavefront sensor, generates a correction signal which is fed to the deformable mirror to compensate for the measured phase aberrations. As discussed in column 7, lines 14-37, after correction has been achieved via the wavefront sensing of the reflected retinal laser-based point source, a high-resolution image of the retina can be acquired by imaging a krypton flash lamp onto the eye's pupil and directing the reflected image of the retina to the deformable mirror, which directs the reflected image onto a second CCD camera body for capture. Examples of prior art Schack-Hartmann wavefront sensors are described in U.S. Pat. Nos. 4,399,356; 4,725,138, 4,737,621, and 5,529,765; each herein incorporated by reference in its entirety.

Notably, the retinal imaging method and apparatus of Williams and Liang, supra, utilizes two different light sources—a laser light source and a krypton flash lamp—to perform the wavefront measurement and correction operations and imaging operations. Such a design significantly increases the complexity and cost of the system.

In addition, the retinal imaging method and apparatus Williams and Liang cannot correct for aberrations (such as those due to blinking or accommodation) that occur after the wavefront sensing and compensation operations are complete (for example, during the subsequent imaging operations).

In addition, the retinal imaging method and apparatus of Williams and Liang does not permit the user to view (observe) the ocular fundus through a view finder, which limits the applications of the retinal imaging method and apparatus of Williams and Liang.

In addition, the Schack-Hartmann wavefront sensor of the retinal imaging apparatus of Williams and Liang is susceptible to the dot crossover problem. More specifically, in a highly aberrated eye, the location of spots produced on the CCD camera body may overlap (or cross). Such overlap (or crossover) introduces an ambiguity in the measurement that must be resolved, or an error will be introduced.

Other ophthalmic imaging instruments (such as corneal topographers, retinal topographers, corneal imaging devices and retinal imaging devices) suffer from these same limitations. A corneal topographers is an ophthalmic instrument that projects light (such as a series of illuminated rings or light slits) onto the anterior corneal surface, which are reflected back into the instrument. The reflections are analyzed by the instrument and a topographical map of the anterior surface of the cornea (and possibly of the posterior surface and thickness of the cornea) is generated. The topographical map and computerized analysis reveals any distortions of the cornea. Alternatively, corneal topographers may use optical coherent tomography to image and characterize the thickness of the corneal epithelium and characterize the 3-D structure of the cornea. Retinal topographers utilize similar techniques to characterize the structure of the retina. Corneal imaging devices capture high resolution images (typically utilizing confocal microscopy, such as laser confocal scanning microscopy) of the various portions of the cornea of the human eye. In addition, such corneal imaging devices may derive high resolution tomography of such corneal portions from analysis of the captured images. Retinal imaging devices utilize similar techniques to capture high resolution images of the various portions of the retina of the human eye. In addition, such retinal image devices may derive high resolution tomography of such retinal portions from analysis of the captured images.

In addition, current ophthalmic examination instruments (including retinoscopes, autorefractors, slit lamps and other indirect opthalmoscopes) do not measure and characterize the higher order aberrations of the human eye, which may be required for adequately diagnosing and treating the patient. A retinoscope (or phoropter) is an ophthalmic instrument that subjectively measures the refractive error of the eye. An autorefractor is an ophthalmic instrument that objectively measures the refractive error of the eye. The retinoscope and autorefractor characterize the refractive errors of the eye only in terms of focal power (typically measured in diopter) required to correct for such focal errors. A slit lamp is an ophthalmic instrument that includes a moveable light source and binocular microscope with which the practitioner can examine the eye. It is used by itself to evaluate the anterior segment of the eye, and when combined with special lenses, adapts for examination of the posterior segment of the eye. An indirect opthalmoscope is an ophthalmic instrument that allows the observer to gain a view of the cornea, retina or other portion of the eye. A light source from the indirect opthalmoscope is directed into the patient's eye and the reflected light is gathered by a condensing lens to form an image of the patient's eye under observation. This image is viewed by the practitioner through a view finder and/or through image capture and display.

Thus, there is a great need in the art for an improved ophthalmic instruments, including ophthalmic imaging instruments and ophthalmic examination instruments, that avoid the shortcomings and drawbacks of prior art ophthalmic instruments.

OBJECTS AND SUMMARY OF THE INVENTION

Accordingly, a primary object of the present invention is to provide improved ophthalmic instruments, including ophthalmic imaging instruments and ophthalmic examination instruments, that are free of the shortcomings and drawbacks of prior art ophthalmic instruments.

Another object of the present invention is to provide an improved ophthalmic imaging instrument for capturing high resolution images of the eye wherein a wavefront sensor-based adaptive optical subsystem is provided for measuring phase aberrations in reflections derived from light produced by an imaging light source (e.g., flash lamp) and compensating for such phase aberrations when capturing images of the human eye derived from light produced by the same imaging light. The high-resolution image data captured (and stored) by the improved instrument may be used to assist in detection and diagnosis of abnormalities and disease in the human eye and treatment (including pre-surgery preparation and computer-assisted eye surgery) of abnormalities and disease in the human eye.

Another object of the present invention is to provide an improved ophthalmic imaging instrument utilizing a single light source to perform wavefront measurement and correction operations and imaging operations, thereby significantly decreasing the complexity and cost of the instrument.

Another object of the present invention is to provide an improved ophthalmic imaging instrument capable of executing in a continuous closed loop fashion, whereby wavefront sensing and compensation is performed during imaging operations, thereby enabling the system to correct for aberrations (such as those caused by blinking or accommodation) that occur after an initial wavefront sensing and compensation operations are complete (for example, during the subsequent imaging operations).

Another object of the present invention is to provide an improved ophthalmic imaging instrument that performs wavefront sensing (and preferably wavefront compensation) and includes an observation source that is used during an observation mode of operation to view (observe) the eye, which expands the potential useful applications of the instrument.

Another object of the present invention is to provide an improved ophthalmic imaging instrument with a Schack-Hartmann wavefront sensor that includes a mechanism to resolve dot crossover problems for highly aberrated eyes, thus providing an improved dynamic range of operation that enables measurement of an important class of eye aberrations.

Another object of the present invention is to provide an improved ophthalmic imaging instrument of modular construction with an optical subsystem, wavefront sensor-based optical subsystem and imaging subsystem packaged in separate and distinct modular housings that interface via detachable connectors. In addition, the optical components of these modules are designed such that either the wavefront sensor-based adaptive optical subsystem or the imaging subsystem can be selectively interfaced directly to the optical subsystem (or directly to a relay lens adapter). Alternatively, the wavefront sensor-based optical subsystem and imaging subsystem may be packaged together in a module housing separate and distinct from a module housing for the optical subsystem and interfaces thereto by detachable connectors. Such modular designs enables flexibility in meeting changing user demands.

Another object of the present invention is to provide an improved wavefront sensor-based ophthalmic instrument that measures the high order aberrations of the human eye and generates data graphically representing such high aberrations (such as graphical representations of the OPD function of the eye) and supplies such data to a display interface, which operates to display such graphical representations on a display device (for example, a TFT LCD device) for view by the practitioner. Such graphical representations provide the practitioner with valuable information characterizing the high order optical errors of the eye (which is far beyond the diopter information typically provided by current ophthalmic instruments) for use in diagnosis and treatment of abnormalities and disease in the eye.

Another object of the present invention is to provide an improved wavefront sensor-based ophthalmic instrument configured as a desktop instrument.

Another object of the present invention is to provide an improved wavefront sensor-based ophthalmic instrument configured as a hand-held instrument.

Another object of the present invention is to provide an improved wavefront sensor-based ophthalmic instrument configured as a hand-held binocular instrument.

Another object of the present invention is to provide an improved ophthalmic instrument having a wavefront-sensor based subsystem that forwards data representative of the high order aberrations of human eye measured therein to a lens fabrication system which fabricates lens (such as contact lens or custom glasses) that compensate for such high order aberrations.

Another object of the present invention is to provide an improved ophthalmic instrument having a wavefront-sensor based subsystem that forwards data representative of the high order aberrations of the human eye to a computer-based ophthalmic surgery system (such as a laser refractive surgery system) such that it compensates for such aberrations when surgically treating the human eye.

Another object of the present invention is to provide an improved ophthalmic instrument having a wavefront-sensor based subsystem that provides data representative of the high order aberrations of human eye measured therein to a practitioner to aid in the diagnosis and/or treatment of the eye.

These and other objects of the present invention will become apparent hereinafter and in the Claims to Invention.

BRIEF DESCRIPTION OF THE DRAWINGS

For a more complete understanding of the present invention, the following Detailed Description of the Illustrative Embodiment should be read in conjunction with the accompanying Drawings.

FIG. 9B is a schematic representation illustrating the configuration of the wavefront sensor-based ophthalmic instrument as a hand-held instrument according to the present invention.

DETAILED DESCRIPTION OF THE BEST MODE EMBODIMENTS OF THE INVENTION

Figure 1:
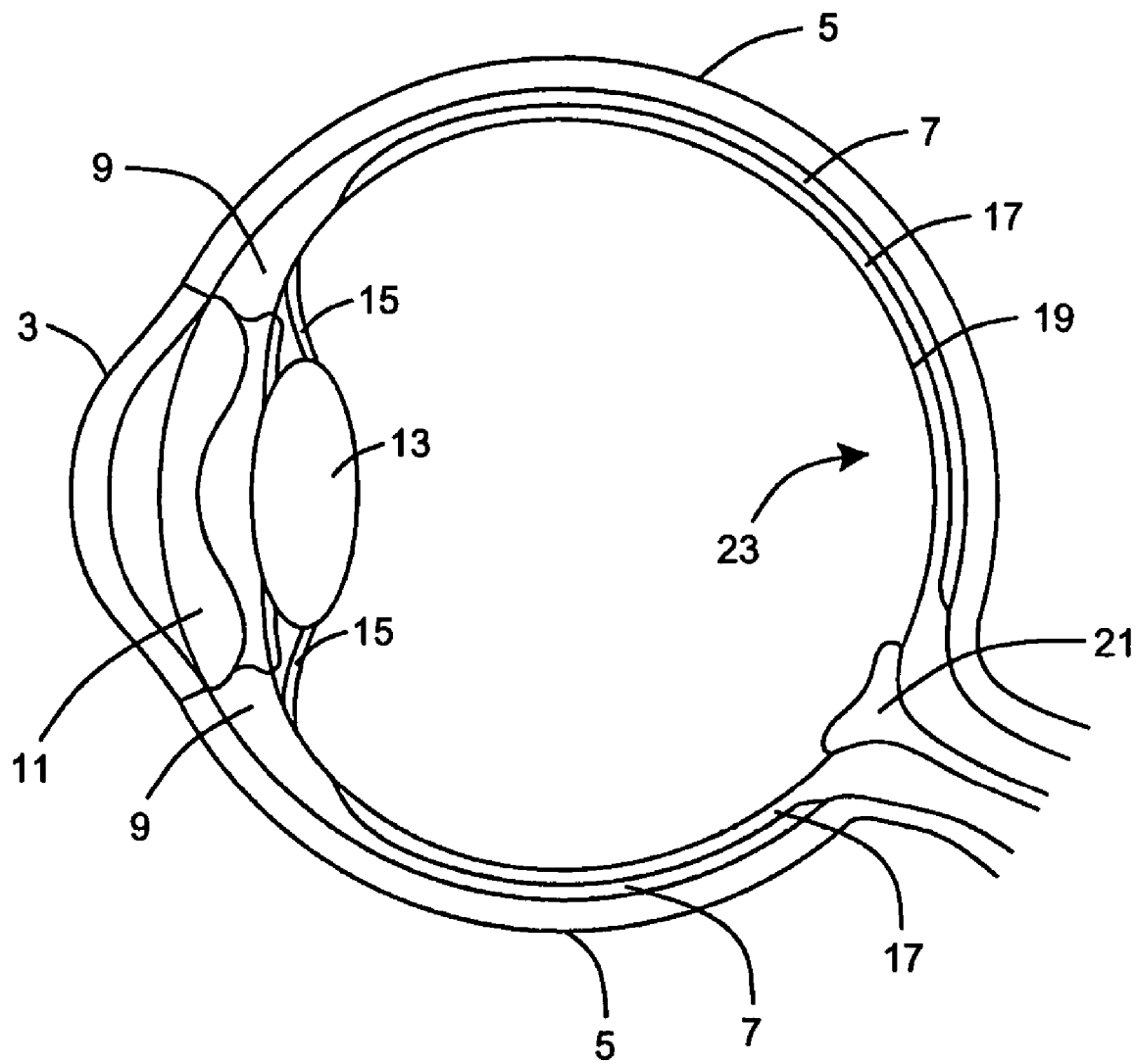
FIG. 1 is a pictorial illustration of a horizontal cross section of the human eye.

Referring to the figures in the accompanying Drawings, the preferred embodiments of the ophthalmic instruments of the present invention will be described in greater detail, wherein like elements will be indicated using like reference numerals.

According to the present invention, an ophthalmic imaging instrument includes a wavefront sensor-based adaptive optical subsystem that measures phase aberrations in reflections derived from light produced by an imaging light source and compensates for such phase aberrations when capturing images of reflections derived from light produced by the same imaging light source. For descriptive purposes, the wavefront sensor-based adaptive optical ophthalmic imaging instrument as described below comprises a fundus camera; however the present invention is not limited in this respect and is broadly applicable to any ophthalmic imaging instrument that captures images of the eye, including corneal topographer, retinal topographer, corneal imaging device, and retinal imaging device. In addition, other aspects of the present invention are broadly applicable to ophthalmic instruments, including ophthalmic examination instruments such as retinoscopes, autorefractors, slit lamps or other indirect opthalmoscopes.

Figure 2A:
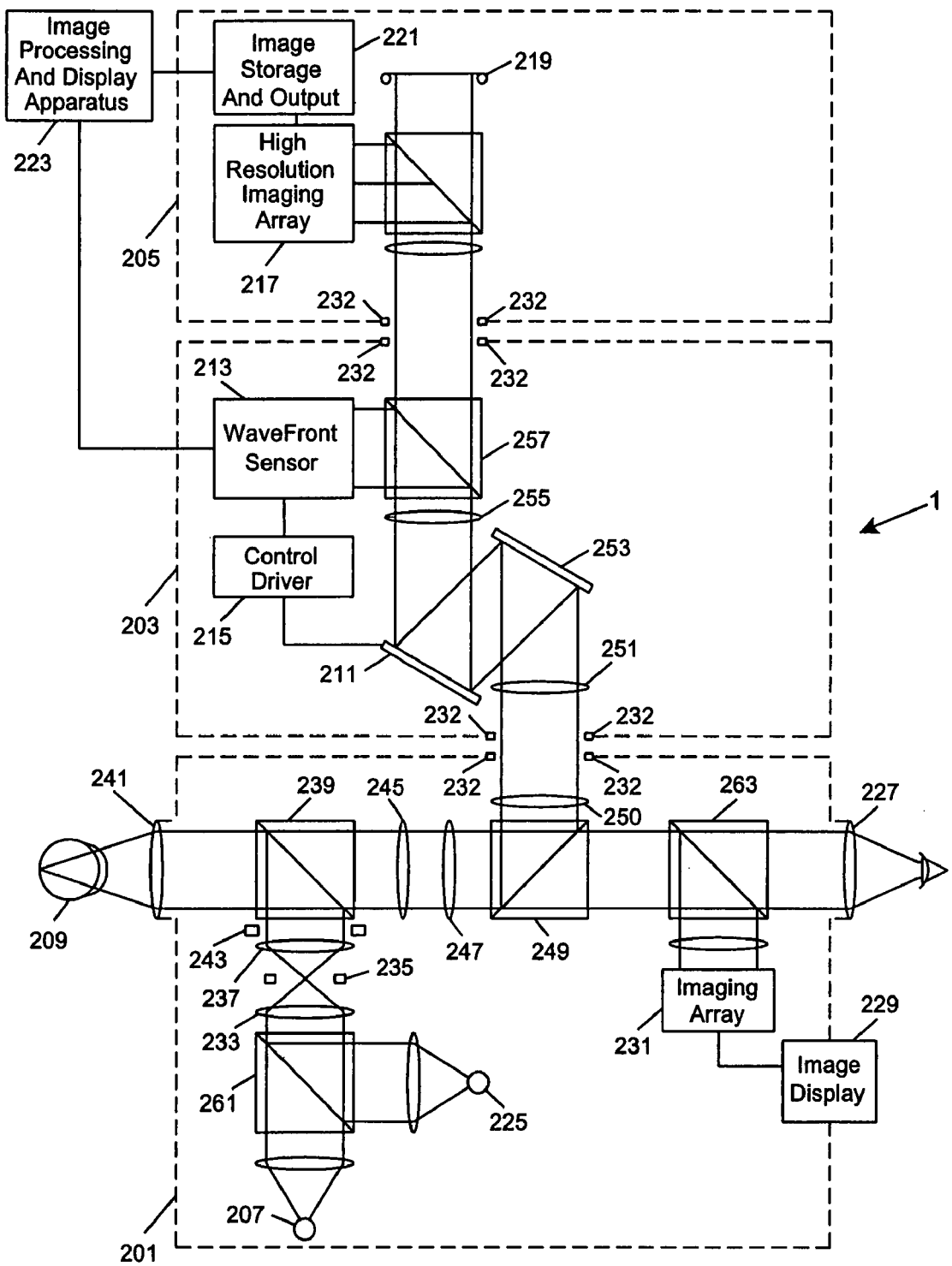
FIG. 2A is a schematic representation of an exemplary embodiment of the ophthalmic imaging instrument (e.g., fundus camera) of the present invention, which provides high-resolution imaging of the human eye.

Referring now to FIG. 2A, there is shown, in schematic form, an exemplary embodiment of the fundus camera 1 according to the present invention, which provides high-resolution imaging of the ocular fundus 23 of a subject eye 209. As shown, the fundus camera 1 includes an optical subsystem 201 having an imaging light source 207 (e.g., a flash source such as xenon flash lamp or krypton flash lamp or a laser light source) that is used during an imaging mode of operation to capture on film 219 and/or on an imaging device 217 (such as CCD camera body or integrating CCD camera body or CMOS camera body) an image of the ocular fundus (or portion thereof) of the subject eye 209. The optical subsystem 201 includes optical elements (such as lens, diaphragm and beam splitter(s)) that image the light produced by the imaging light source 207 onto the pupil of the subject eye 209, collect and collimate the light reflected from the retina of the subject eye 209, and direct such collimated light to the wavefront sensor-based adaptive optical subsystem 203. In addition, the optical subsystem 201 preferably includes an internal fixation target (not shown) that is a pointer moveable into the optical path of the camera 1 such that the user and the patient can see it. The patient is instructed to look at the tip of the pointer as the user moves it to align the patient's eye. In addition, it may be used to adjust accommodation of the lens of the subject eye 209 such that it is focused at various depths of view, including at (or substantially near) infinity.

Figure 2B:
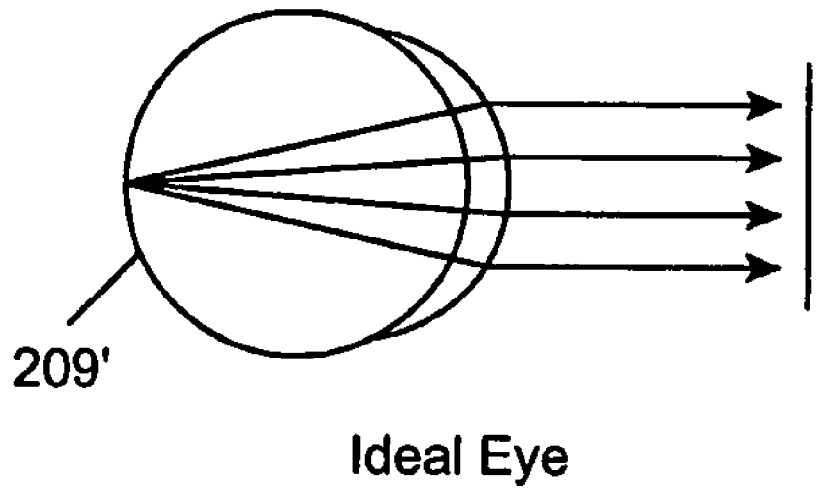
FIG. 2B is a schematic illustrating depicting the planar wavefront and distorted wavefront produced via reflection of a point source imaged onto the ocular fundus of an ideal eye 209' and an aberrated eye 209", respectively.
Figure 2B:
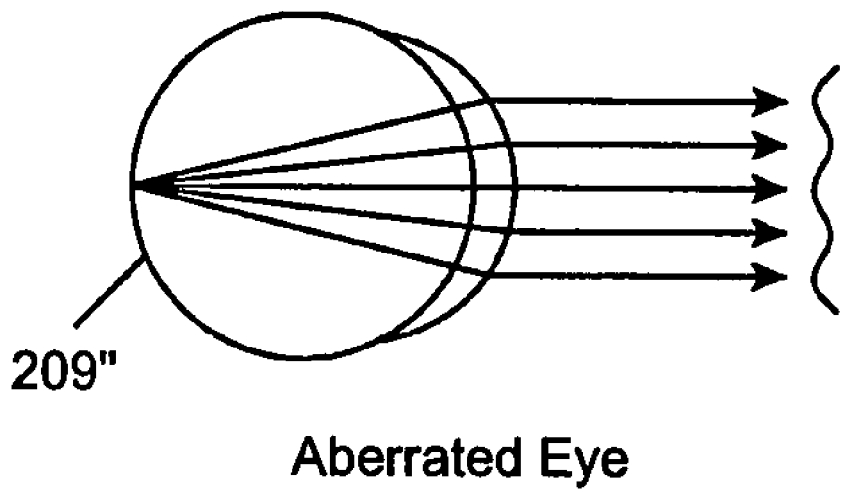

The light produced from the imaging light source 207 forms planar (e.g., phase-aligned) wavefronts that are directed to the pupil of the subject eye. These planar wavefronts are imaged onto the retina of the subject eye by the crystalline lens substantially as a point source. As illustrated in FIG. 2B, the light reflected from the retina of an ideal subject eye 209' forms planar wavefronts at the pupil of the human eye as it leaves the human eye while the light reflected from the retina of an aberrated eye 209" forms distorted wavefronts at the pupil of the human eye as it leaves the human eye. The human eye 209 is not ideal and has some form of aberrations such as defocus (which may be myopia (near-sightedness) or hyperopia (far-sightedness)) and astigmatism as well has many other higher order optical aberrations.

The optical elements of the optical subsystem 201 and wavefront sensor-based adaptive optical subsystem 203 recreate these distorted wavefronts in the plane of a phase-compensating optical element 211 (such as a deformable mirror or liquid crystal device) and in the plane of a wavefront sensor 213 (such as a Schack-Hartmann wavefront sensor). The wavefront sensor 213 measures the phase aberrations in the distorted wavefronts imaged thereon. The phase aberrations measured by the wavefront sensor 213 represent the aberrations of the subject eye (including high order aberrations of the eye such as spherical aberration, astigmatism and coma). The wavefront sensor 213 operates in a closed-loop fashion with a controller/driver 215 to control the phase-compensating optical element 211 to compensate for such phase aberrations to restore the distorted wavefronts to phase-aligned wavefronts, which are directed to the wavefront sensor 213 (for further wavefront measurement and compensation if required) and the imaging subsystem 205. Exemplary control schemes that may be implemented by the controller/driver 215 to control the phase-compensating optical element 211 to compensate for such phase aberrations are described by Tyson in "Introduction to Adaptive Optics," SPIE Press, 2000, pgs. 93-109.

The wavefront sensor 213 preferably communicates to an image processing and/or display apparatus 223 (such as a computer workstation) that displays to the operator/observer a graphical user interface (GUI) for alignment and calibration of the wavefront sensor 213. Examples of such alignment and calibration operations for a Schack-Hartmann wavefront sensor are described below with respect to FIGS. 4 and 5, respectively.

The imaging subsystem 205 includes a high-resolution imaging device 217 (such as a CCD camera body or integrating CCD camera body or CMOS camera body) and/or a photographic film unit 219 that captures an image of the restored (phase-aligned) wavefronts produced by the wavefront sensor-based adaptive optical subsystem 203. An image storage and output device 221 is operably coupled to the imaging device 217 to thereby store the image data captured by the imaging device 217. In addition, the image storage and output device 221 preferably communicates (for example, over a high speed serial link such as a USB bus) with the image processing and/or display apparatus 223 (which is non-integral to the subsystems 201, 203 and 205 as shown) to output the image data stored therein for display, printing and image processing operations performed by the image processing and display apparatus 223. Alternatively, the image processing and/or display apparatus 223 may be integral to any one of the subsystems 201, 203 and 205.

In addition, the fundus camera 1 of the present invention preferably includes the following components (which, while not shown in FIG. 2A in order to simplify the diagram, are assumed provided in the system described herein):

Headband and chinrest: the patient is positioned at the camera with his forehead against the band and his chin in the chinrest.

Chinrest adjusting knob: the vertical distance between the forehead band and the chinrest is adjusted with this knob. Positioning of the patient's head is critical to efficient retinal photography. Even small movements of the head affect proper alignment.

External fixation target: The patient views this small swivel light with the fellow eye (the eye not being photographed). The light is positioned such that the view of the eye being photographed is optimized as it changes position with the fellow eye which is tracking the fixation target.

Diopter compensation knob: The normal setting is used for retinal photography of the "normal" eye. Other settings compensate for high myopes, high hyperopes, and for anterior photography.

Angle or magnification lever: A lever that cooperates with optical elements of the optical subsystem 201 to select one of many different view angles (such as between a 50 degree, 35 degree, or 20 degree angle of view). In the wide-angle view (e.g., the 50 degree view) more area of the retina is visible. However, with the wide-angle view structures such as the macula and optic nerve appear smaller in the frame (less magnified). In the narrow angle field of view (e.g., the 20 degree view), retinal structures are larger in the frame (more magnified).

Focusing knob(s): knob(s) that cooperate with the optical elements of the optical subsystem 201 to adjust focus of the fundus camera 1.

Shutter release button: This button fires the imaging light source 207 for imaging operations.

Control lever(s): This lever (or joystick(s)) controls forward/backward, side-to-side, and vertical alignment of the camera. Gross alignment of the camera is accomplished by sliding the base of the camera in the desired direction.

Lamphousing: A removable cover that gives access to bulb(s) for the imaging light source 207 and possibly the observation light source 225.

Filter knob: Various filters can be dialed into the optical path of the fundus camera 1 using this knob. The most commonly used is the green filter (red free) which is used with black-and-white film to accentuate blood vessels.

Illumination diaphragm lever: This lever cooperates with the diaphragm 243 of the optical subsystem 201 to control illumination of the retina.

Tilting handle: This device is used to tilt the camera upward and downward. This is used in situations where the subject (e.g. a nevus or melanoma) is so far out in the periphery that the eye cannot be sufficiently aligned by using the external fixation device alone. The camera can also be rotated left and right along the axis of the base.

Data display: Displays information such as the counter, the timer, and the angle of view being used.

Flash intensity panel: Flash intensity is changed by using the up and down buttons on the panel. The higher the number is, the brighter the flash.

Data switch: Photographs the patient information when pressed. Information such as name, number, and date can be written on a data plate and inserted into the light path.

Timer switch: Used to start and stop the fluorescein angiography timer. The time is recorded on each frame.

Exciter and Barrier switch: Used to insert and remove these filters which are used for fluorescein angiography.

Illumination adjustments: These adjustments control the brightness of the observation light source. This is the light that allows you to see into the eye before you capture a picture with the flash.

Flicker switch: This switch changes the external fixation light into a flickering light. The flickering light is sometimes easier for the patient to identify and follow.

The high-resolution image data captured (and stored) by the imaging subsystem 205 of the fundus camera 1 may be used to assist in detection and diagnosis (such as color imaging, fluorescein angiography, indocyanine green angiography) of abnormalities and disease in the subject eye 209 and treatment (including pre-surgery preparation and computer-assisted eye surgery such as laser refractive surgery) of abnormalities and disease in the subject eye 209.

Such high resolution image data (and pictures) reveal details of the structure of the retina that are not possible to obtain without the use of the wavefront sensor-based adaptive optical subsystem. Moreover, provided with such high-quality images (and pictures), practitioners can detect diseases earlier. For example, glaucoma damage can be detected only after prolonged destruction of the retina's nerve fiber layer. Such high quality images (and pictures) enable a practitioner to view details of the retina's nerve fiber layer for early detection of glaucoma. In addition, such high quality images (and pictures) enable practitioners to chart more precisely the retinal blood vessel damage resulting from diabetes and other diseases.

The optical subsystem 201 of the fundus camera 1 of the present invention preferably includes an observation light source 225 (e.g., a halogen lamp or one or more infra-red light emitting diodes) that is used during an observation mode of operation (which is distinct from the imaging mode of operation) to view (observe) the ocular fundus (or portions thereof)

of the subject eye 209 through a view finder 227 and/or through an image display 229 (such as a TFT LCD device), which is operably coupled to an imaging device 231 (such as a CCD camera body or CMOS camera body). In the observation mode of operation, the optical elements of the optical subsystem 201 image the light produced by the observation light source 225 onto the pupil of the subject eye 209, collect and collimate the light reflected from the retina of the subject eye 209, and direct such collimated light to the view finder 227 and/or to the imaging device 231 (for display on the image display 229).

The optical subsystem 201, wavefront sensor-based optical subsystem 203 and imaging subsystem 205 are preferably packaged in separate and distinct modular housings that interface via detachable connectors 232 as shown in FIG. 2A. In addition, the optical components of the modules are designed such that either the wavefront sensor-based adaptive optical subsystem 203 or the imaging subsystem 205 can be selectively interfaced directly to the optical subsystem 201 (or directly to a relay lens adapter, which houses relay lens 250, that is detachably interfaced to the housing of the optical subsystem 201). Such a modular design enables flexibility in meeting changing user demands. For example, a user might purchase only the optical subsystem 201 and imaging subsystem 205 and configure the system such that the imaging subsystem 205 is interfaced directly to the optical subsystem 201 (or the relay lens adapter). Such a configuration can then be updated by acquiring the wavefront sensor-based adaptive optical subsystem 203 and interfacing the wavefront sensor-based adaptive optical subsystem 203 between the imaging subsystem 205 and the optical subsystem 201 (or the relay lens adapter) as shown in FIG. 2A.

In an alternate embodiment, the wavefront sensor-based optical subsystem 203 and imaging subsystem 205 may be packaged in a module housing separate and distinct from a module housing for the optical subsystem 201. In this embodiment, the module housing for the wavefront sensor-based optical subsystem 203 and imaging subsystem 205 is interfaced via detachable connectors to the module housing for the optical subsystem 201.

As described above, the optical subsystem 201 of the fundus camera 1 of the present invention includes optical elements that image the light produced by the imaging light source 207 onto the pupil of the subject eye 209, collect and collimate the light reflected from the retina of the subject eye 209, and direct such collimated light to the wavefront sensor-based adaptive optical subsystem 203. An exemplary embodiment of such optical elements as illustrated in FIG. 2A includes a condenser lens 233, ring aperture 235, projection lens 237, diaphragm 243, first beam splitter 239 and objective lens 241 that image the light produced by the imaging light source 207 onto the pupil of the subject eye 209. Light reflected from the retina of the subject eye 209 is collected and collimated by the objective lens 241, first beam splitter 239, focusing lens 245 and imaging lens 247. Second beam splitter 249 and relay lens 250 directs the collimated retinal reflections to the wavefront sensor-based adaptive optical subsystem 203. The relay lens 250 may be a relay lens adapter that is detachably interfaced to the housing of the optical subsystem 201.

From the collimated retinal reflections supplied thereto, the optical elements of the wavefront sensor-based adaptive optical subsystem 203 recreate the distorted wavefronts (formed at the pupil of the subject eye 209) in the plane of phase-compensating optical element 211 and a wavefront sensor 213. An exemplary embodiment of such optical elements as illustrated in FIG. 2A includes relay lens 251, mirror 253, lens 255 and beam splitter 257.

The wavefront sensor 213 of the wavefront sensor-based adaptive optical subsystem 203 preferably comprises a Shack-Hartmann wavefront sensor, which includes an array of small lenslets disposed in front of an imaging device (such as a CCD camera body, integrating CCD camera body or CMOS camera body). The lenslets partition the incident wavefront into a large number of smaller wavefronts, each of which is focused to a small spot on the imaging device. The spatial location of each spot is a direct measure of the local slope of the incident wavefront. The wavefront sensor includes signal processing circuitry that samples the output of the imaging device and processes the data output therefrom to track the spatial positions of these spots to derive the local slope (e.g., local gradients) of the incident wavefronts. These local gradients are reconstructed to form data representative of the aberrations of the distorted wavefronts (including defocus, spherical aberration, coma, astigmatism in addition to other higher order aberrations of the distorted wavefronts). For example, the local gradients may be reconstructed into an optical path difference (OPD) array, which stores a scalar value that represents the optical path difference at each lenslet. Alternatively, the local gradients may be reconstructed into an OPD function, for example, by minimizing the difference between the derivatives of an analytical function (such as a set of Zernike polynomials, Seidel polynomials, Hermites polynomials, Chebychev polynomials, and Legendre polynomials) and the measured local gradients. A more detailed description of an exemplary Shack-Hartman wavefront sensor is described below with respect to FIGS. 3A-(C). Alternate wavefront sensing techniques are described in detail in Geary, "Introduction to Wavefront Sensors", SPIE Optical Engineering Press, 1995, pp. 53-103.

Alternatively, the wavefront sensor 213 may comprise a Tscherning wavefront analyzer that illuminates the subject eye with a dot pattern formed by a laser source and dot pattern mask. The reflected dot pattern is captured by the imaging device and the image data is analyzed to derive deviations in the dot pattern from its ideal locations. From the resulting deviations, aberrations in the distorted wavefronts produced from the subject eye are mathematically reconstructed. A more detailed description of a Tscherning wavefront analyzer is described by Mierdel et al. in "A measuring device for the assessment of monochromatic aberrations of the eye," Ophthamologe, 1997, Vol. 94, pgs. 441-445, and Mrochen et al., "Principles of Tscherning Aberrometry," Journal of Refractive Surgery, Vol. 16, September/October 2000.

Alternately, the wavefront sensor 213 may comprise a spatially resolved refractometer as described in detail by He et al. in "Measurement of the wave-front aberration of the eye by fast psychophysical procedure," J Opt Soc Am A, 1998, Vol. 15, pgs. 2449-2456 and in U.S. Pat. Nos. 5,258,791 and 6,000,800, each incorporated herein by reference in its entirety.

The wavefront sensor 213 measures the aberrations of the distorted wavefronts (including defocus, spherical aberration, coma, astigmatism in addition to other higher order aberrations). The phase aberrations measured by the wavefront sensor 213 represent the aberrations of the subject eye (including high order aberrations of the eye such as spherical aberration, astigmatism and coma). The wavefront sensor 213 supplies data representative of these aberrations (such as an OPD array or OPD function) to the controller/driver 215, which controls the phase-compensating optical element 211 to warp its optical surface (to form the complex conjugate of measured aberrations) to compensate for the aberrations measured by the wavefront sensor, thereby restoring the distorted wavefronts to phase-aligned wavefronts, which are directed to the wavefront sensor 213 (for further wavefront measurement and compensation if required) and imaging subsystem 205.

Figure 6A:
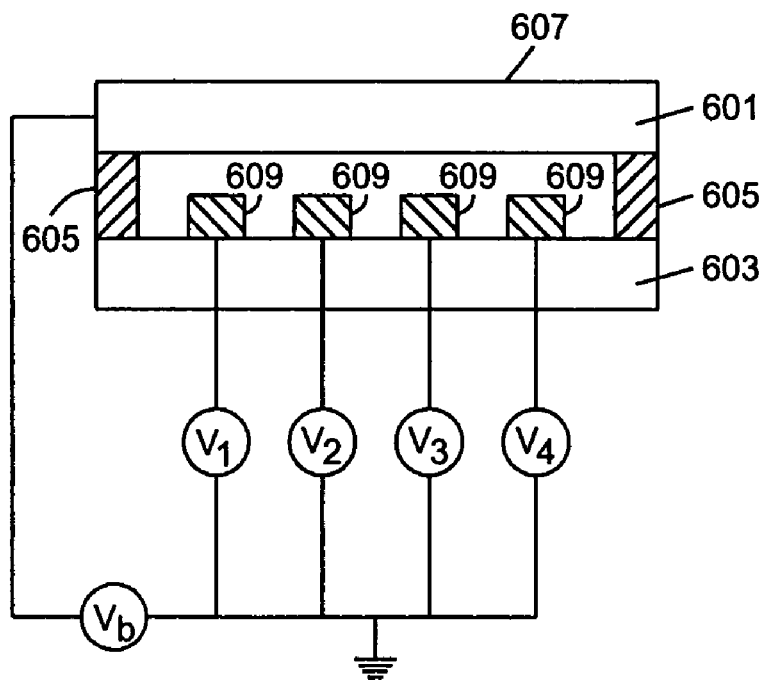
FIG. 6A is a schematic cross section of an exemplary silicon micromachined membrane mirror of the wavefront-sensing based adaptive optical subsystem according to the present invention.
Figure 6B:
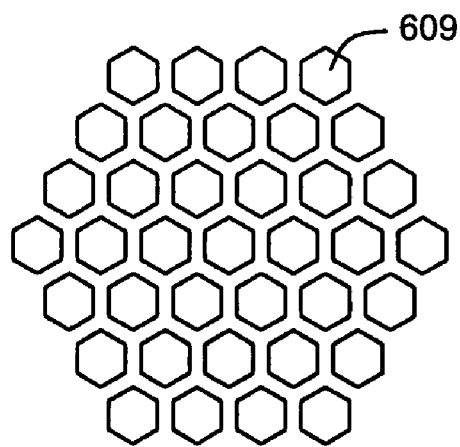
FIG. 6B is pictorial illustration of the control electrode structure of the exemplary silicon micromachined membrane mirror shown in FIG. 6A.

The phase-compensating optical element 211 may comprise a deformable mirror or a liquid crystal device. Silicon micro-machined membrane mirrors (which is a class of deformable mirrors that are readily available, for example, from OKO Technologies of Deelft, the Netherlands) are suitable for phase compensation for many ophthalmic imaging applications. As illustrated in FIG. 6A, such mirrors typically consist of a silicon chip 601 mounted over a printed circuit board substrate 603 by spacers 605. The top surface 607 of the chip 603 contains a membrane (typically comprising silicon nitride) which is coated with a reflective layer (such as aluminum or gold) to form the mirror surface. The printed circuit board 603 contains a control electrode structure (as illustrated in FIG. 6B) that operates to deform the shape of the reflective membrane by applying bias and control voltages to the membrane and the control electrodes 609. Other classes of deformable mirrors (including segmented mirrors, continuous faceplate mirrors, and edge actuated mirrors) suitable for phase compensation for many eye imaging applications are described by Tyson in "Introduction to Adaptive Optics," SPIE Press, 2000, pgs. 83-91, supra.

As described above, the optical elements of the optical subsystem 201 may operate in the observation mode of operation to image light produced by the observation light source 225 onto the pupil of the subject eye 209, collect and collimate the light reflected from the subject eye 209, and direct such collimated light to the view finder 227 and/or the imaging device 231. An exemplary embodiment of such optical elements is illustrated in FIG. 2A, wherein beam combiner 263, condenser lens 233, ring aperture 235, projection lens 237, first beam splitter 239 and objective lens 241 cooperate to image light produced by the observation light source 225 onto the pupil of the subject eye 209. Light reflected from the subject eye 209 is collected and collimated by the objective lens 241, first beam splitter 239, diaphragm 243, focusing lens 245 and imaging lens 247. Second beam splitter 249 directs the collimated reflections to the view finder 227 and/or the imaging device 231. Optionally (in the event that both a view finder 227 and imaging device 231 are used), a third beam splitter 263 directs the collimated retinal reflections to both the view finder 227 and the imaging device 231.

Figure 3A:
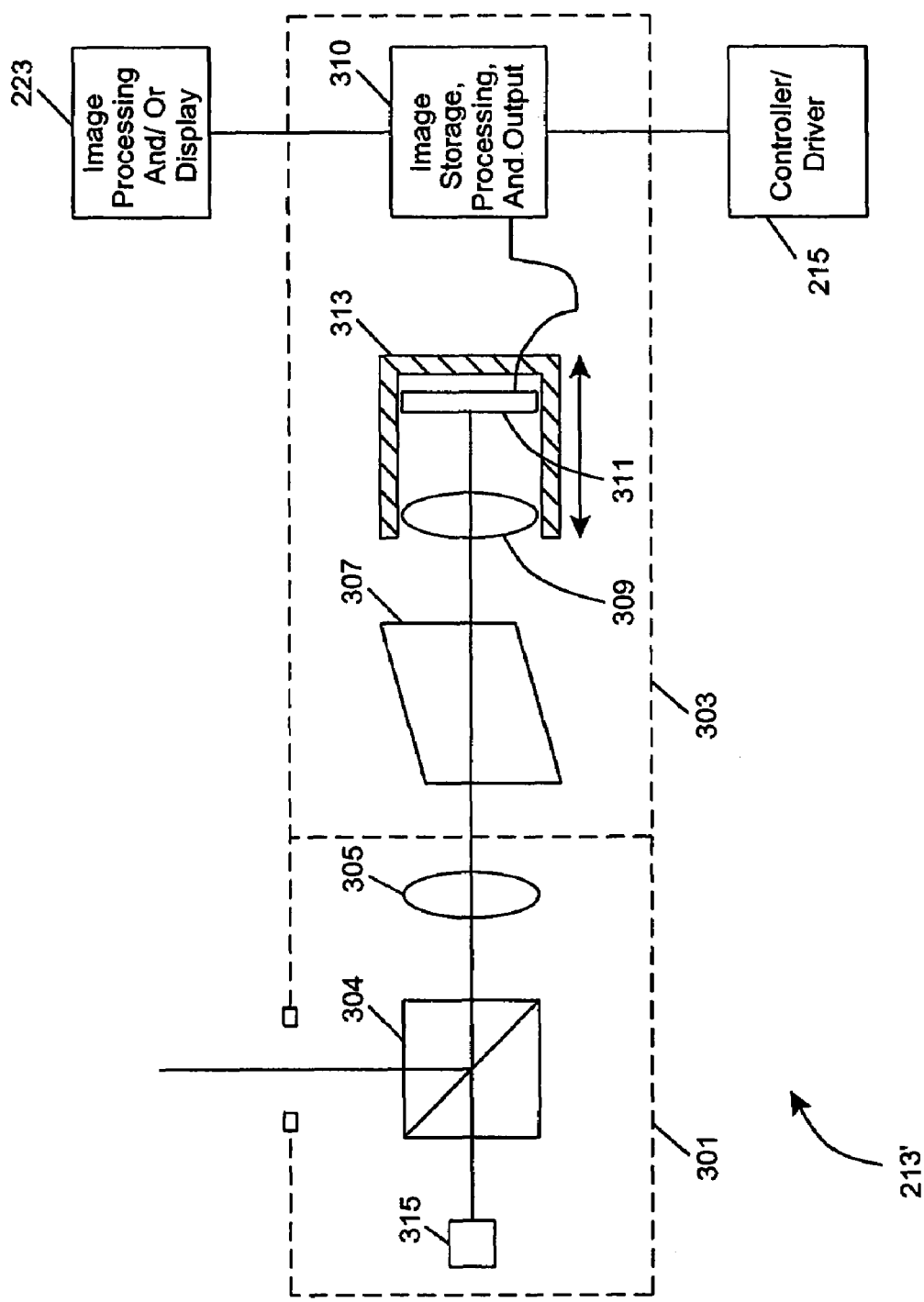
FIGS. 3A-3C are schematic representations of an exemplary embodiment of the Shack-Hartmann wavefront sensing components of the adaptive optical subsystem of the ophthalmic imaging instrument (e.g., fundus camera) shown in FIG. 1 according to the present invention.
Figure 3B:
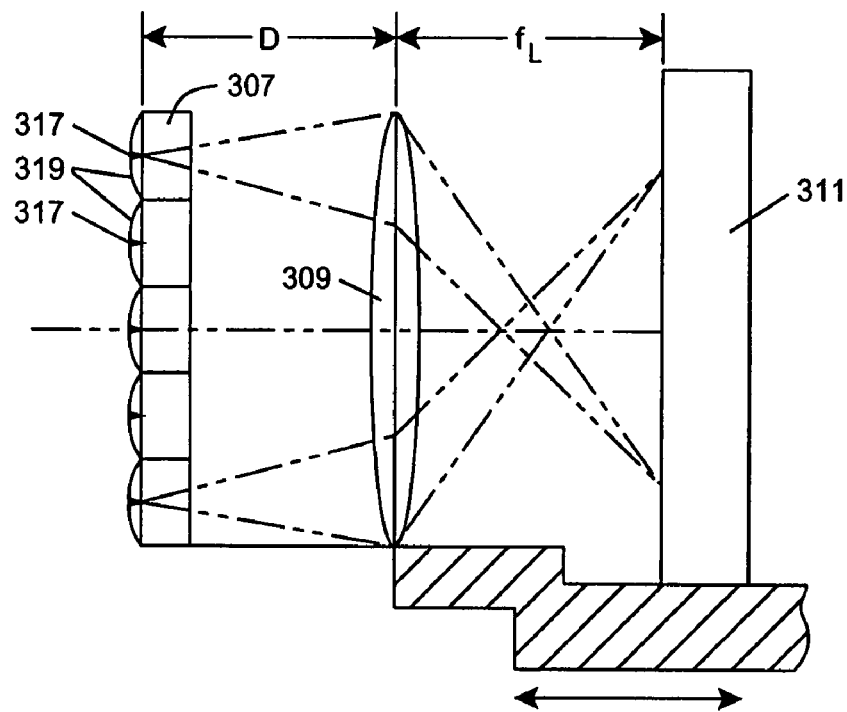
Figure 3C:
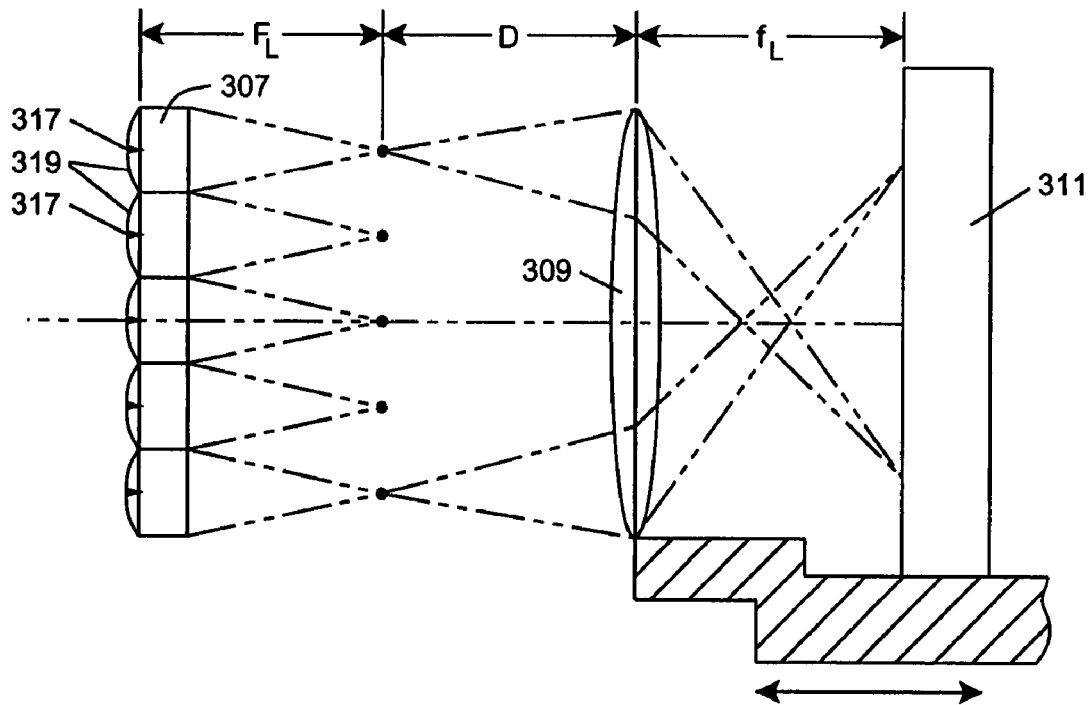

FIGS. 3A-3C illustrate an exemplary embodiment of the Shack-Hartmann wavefront sensing components of the ophthalmic instrument of the present invention. As shown in FIG. 3A, these components include foreoptics 301 and a wavefront sensor head 303. The foreoptics 301 include a beam combiner 304 and collimating lens 305 which operate in conjunction with the optical elements of the instrument (for example, the adaptive optical subsystem 203 and optical subsystem 201) so as to recreate the distorted wavefronts (formed at the pupil of the subject eye 209) in the plane of a lenslet array 307. The lenslet array 307 partitions the incident wavefront into a large number of smaller wavefronts, each of which is focused by a relay lens 309 to a small spot on an imaging device 311 (mounted within an optical device 313 such as a CCD camera body, a CMOS camera body, or an integrating CCD camera body). The imaging device 311 is operably coupled to an image storage, processing and output device 310 that grabs the image data captured by the imaging device 311, processes the grabbed image data to track test spot movements, derives a measure of the phase aberrations of the distorted wavefronts (including defocus, spherical aberration, coma, astigmatism in addition to other higher order aberrations of the distorted wavefronts) from such test spot movements, and possibly stores such image data in persistent storage. In addition, the image storage, processing and output device 310 generates data representative of the aberrations of the distorted wavefronts (such as an OPD array or OPD function) from such measures. In adaptive optical applications, such data is provided to controller/driver 215, which controls a phase-compensating optical element to compensate for such phase aberrations to restore the distorted wavefronts to phase-aligned wavefronts, which may be directed to an imaging subsystem for capture.

In addition, the image storage, processing and output device 310 of the sensing head 303 preferably interfaces to image processing and/or display apparatus 223 that displays a graphical user interface for alignment and calibration of the wavefront sensing head 303. Examples of such alignment and calibration operations are described below with respect to FIGS. 4 and 5, respectively.

The test spot pattern is formed at approximately a lenslet focal length behind the lenslet array 307. For a number of reasons, it is desirable to use the relay lens 309 to relay that test spot pattern onto the imaging device 311. First, this allows the matching of the scale of the test spot pattern to the pixel size of the imaging device 311. Second, it simplifies the implementation of interchangeable lenslets (of varying focal length and/or aperture size). Finally, it allows the wavefront sensor head 303 to gather a much wider range of data on the optical system under test and, as a result, make measurements of greater accuracy. Preferably, the relay lens 309 operates in a telecentric mode to minimize the possibility of magnification errors that lead to wavefront estimation errors.

The Shack-Hartmann wavefront sensor head 303 inherently performs a differential measurement. The basic quantity measured by the sensor 303 is the position of spots formed on the imaging device 311. Since that position depends upon the particular geometry of the sensor head and its optics, there must be some geometric reference of the nominal null. This geometric reference may be provided by a reference plane wave (generated by a laser source and suitable collimating optical elements) that is recreated at the plane of the lenslet array 307 to establish a reference spot pattern captured by imaging device 311. Locations of the reference spots are derived from the reference spot pattern and recorded by the image storage processing and output device 310. Deviation of test spot location (with respect to the recorded reference spot location) is measured during wavefront sensing operations to measure the phase aberration in the wavefront sampled by the corresponding lenslet. This approach is costly because the flat wave signal source and collimating optics must be of high optical quality.

An alternate approach achieves this geometric reference (e.g., reference spot pattern) internally (without the costs of a high quality flat wave signal source and collimating optics) by providing a substantially-opaque element at the center of each lenslet of the lenslet array 311. A more detailed description of this approach is described in PCT Publication WO 97/21989, incorporated herein by reference in its entirety. As illustrated in FIGS. 3B and 3C, the opaque element, sometimes referred to as a reference fiducial point 317, is accurately positioned at the optical axis of the given lenslet 319 at the location of the chief ray of the lenslet 319. In addition, the relay lens 309 and the imaging device 311 are mounted on a linear actuator, which preferably has sufficient travel to allow the imaging device 311 to image all planes from the plane substantially near the lenslet array 307 itself, back to the focal plane of the longest focal length lenslet array. For the sake of description, the focal length of the individual lenslets 317 of the lenslet array 307 is shown as $f_L$, the focal length of the relay lens 309 is shown as $F_L$, and the object distance of the relay lens is shown as D.

The reference spot pattern (i.e., locations of the reference spots) is measured and recorded by: (i) moving the relay lens 309 and imaging device 311 to a position whereby the fiducial points are imaged onto the imaging device 311 (i.e., the plane of the lenslet array 307 and the plane of the relay lens 309 is offset by D as shown in FIG. 3B), (ii) illuminating the lenslet array 307 with a reference beam, and (iii) controlling the image storage processing and output device 310 to grab the image captured by the imaging device 311 and process this image to identify locations of the reference spots that make up the reference spot pattern. The reference beam is produced by a reference source 315 and directed to the lenslet array 307 by beam combiner 304 and collimating lens 305 as shown in FIG. 3A. Advantageously, these optical components may be of lower optical quality and costs than the optical components required to provide the flat reference wave as discussed above.

In this approach, the phase aberration in the distorted wavefront sampled by a given lenslet is approximated by determining the location of the test spot produced by the given lenslet relative to the location of the reference spot corresponding to the given lenslet. This measurement is accomplished by moving the relay lens 309 and imaging device 311 to a position whereby the focal plane of the lenslet array 307 is imaged onto the imaging device 311 (i.e., the plane of the lenslet array 307 and the plane of the relay lens 309 is offset by ($F_L$+D) as shown in FIG. 3C), recreating the distorted wavefront at the plane of the lenslet array 307, controlling the image storage processing and output device 310 to: (i) grab the image captured by the imaging device 311, (ii) process this image to identify the location of the test spot for the given lenslet, and (iii) compute the relative difference between this test spot location and the location of the reference spot for the given lenslet.

Proper alignment (and focus) of the optical elements of subsystems 201, 203 and 205 and calibration of the wavefront sensor is required for optimal imaging operations. In addition, proper alignment of the subject eye to the fundus camera 1 (or proper alignment of the camera 1 to the subject eye) is also required for optimal imaging operations.

Preferably, alignment of the optical elements of subsystems 201, 203 and 205 is accomplished by user manipulation of one or more control levers (or joystick(s)) that control forward/backward, side-to-side, and vertical alignment of the optical elements of the camera 1. Gross alignment of the camera 1 is preferably accomplished by sliding the base of the camera 1 in the desired direction. Focus of the camera is preferably controlled by one or more focusing knobs that cooperate with the optical elements of the optical subsystem 201 to adjust focus of the camera 1.

For the Shack-Hartmann wavefront sensor 303 of FIGS. 3A-(C), the purpose of alignment is twofold. The primary purpose is to locate the wavefront sensing head in space so that the object under test (e.g., the collimated retinal reflections produced by the optical subsystem 201 of FIG. 2A) will be roughly centered on the lenslet array 307 of the wavefront sensing head 303 and approximately aligned with the optical axis of the lenslet array 307 (and the relay lens 309 and imaging device 311). The second purpose is to verify that wavefront sensing head 303 is actually looking at what it should be looking at. A more detailed description of an illustrative procedure for alignment the Shack-Hartmann wavefront sensing head 303 of FIGS. 3A-(C) is described below with respect to the flow chart of FIGS. 4A and 4B.

The purpose of calibration of the Schack-Hartmann wavefront sensing head 303 is to determine the conversion factor between spot motion for a given lenslet and local wavefront tilt at the lenslet. This conversion factor is dependent upon the distance between the pupil image plane and the spot image plane, and the radius of the pupil of the lenslet (and possibly the refractive index of the lenslet). A more detailed description of the construction for relating spot motion to local wavefront tilt is described in detail by Geary in "Introduction to Wavefront Sensors", SPIE Optical Engineering Press, 1995, pp. 14-20. The distance between the pupil image plane and the spot image plane is set by the distance that the moveable stage (i.e., the relay lens 309 and imaging device 311) moves from the pupil image plane to the spot imaging plane, and the radius of the pupil of the lenslet is set by the size of the individual lenslet elements. Since both of these quantities are determined at the time of manufacture, this basic calibration need not be re-measured each time the system is used. There are, however, a number of parameters related to a particular wavefront measurement that must be determined before that particular wavefront measurement can be made. These include the position of the image of the system pupil (e.g., the image of the retina under test) in the local coordinate system of the wavefront sensing head 303, and the positions of the reference spots. In addition, it is preferable that the system employ a mechanism that can dynamically identify the sub-arrays (pixel areas) of the imaging device 311 that will be used for the determination of both reference spot positions and test spot positions for a particular wavefront measurement in a manner that addresses the dot crossover problem as discussed above. A more detailed description of an illustrative procedure for determining these calibration parameters (including a dynamic mechanism that addresses the dot crossover problem) of the Shack-Hartmann wavefront sensing head 303 is described below with respect to the flow chart of FIG. 5.

Finally, proper alignment of subject eye to the fundus camera 1 may be accomplished with a headband and chin rest whereby the patient is positioned at the camera 1 with his forehead against the headband and his chin in the chinrest. One or more adjusting knobs may be used to adjust the position of the subject eye such that it is properly aligned with the optical axis of the camera 1.

Alternatively, the position (and orientation) of the fundus camera may be changed such that it is properly aligned with the subject eye. This step is suitable for handheld ophthalmic devices. Such alignment is preferably accomplished through the use of cross-hairs and an infrared distance detector embodied within the camera. The cross-hairs are centered in the field of view of the camera and viewable to the user such that the user can accurately position the cross hairs onto the pupil of the subject eye. The infrared distance detector provides visible feedback (i.e., varying frequency flicker lights) or audible feedback (different pitched beeps) that enables the user to accurately position and orient the optical axis of the camera 1 with respect to the subject eye.

Figure 4A:
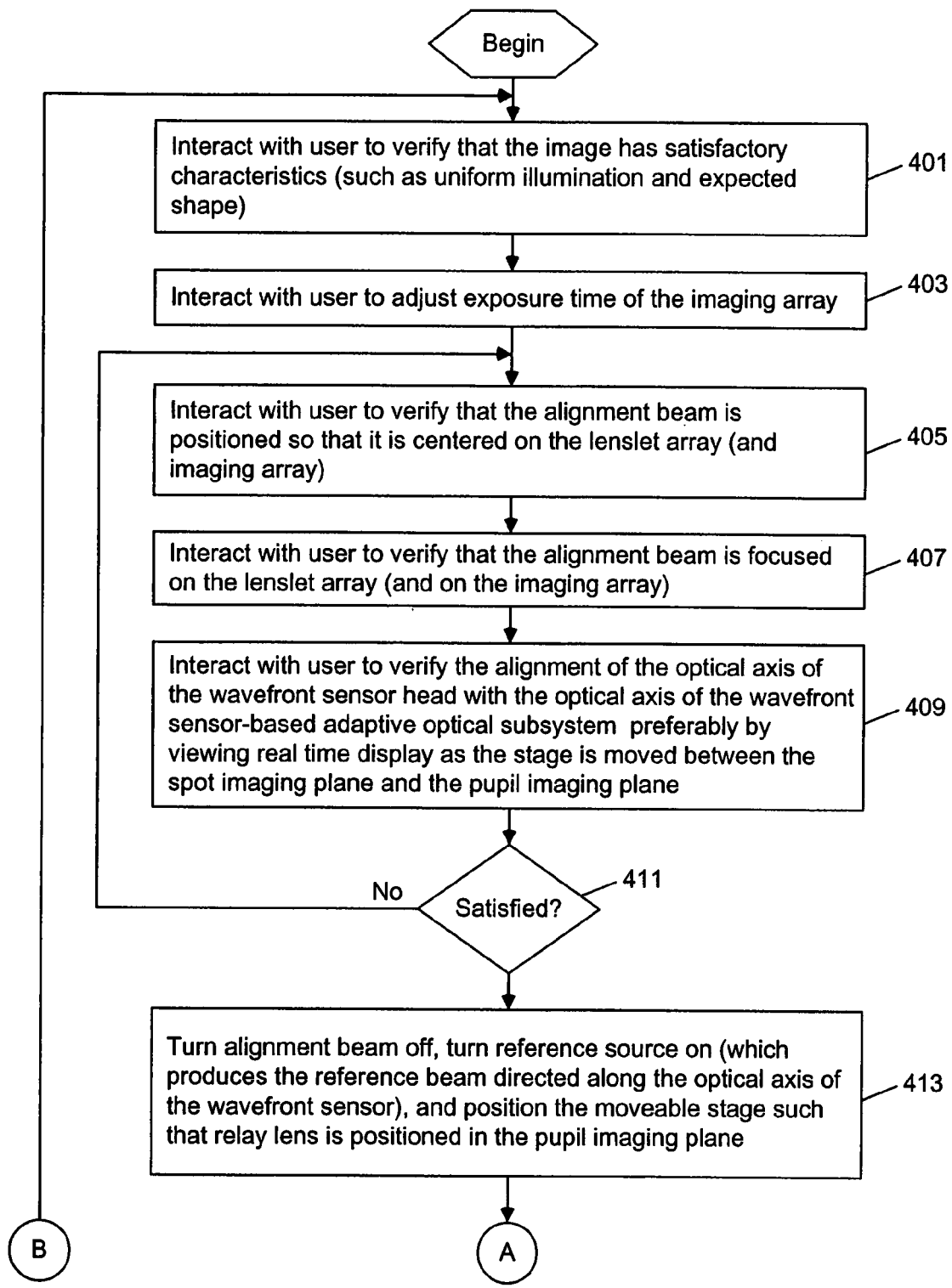
FIGS. 4A and 4B, taken together, set forth a flow chart illustrating exemplary operations for aligning the Shack-Hartmann wavefront sensing components shown in FIGS. 3A-(C).
Figure 4B:
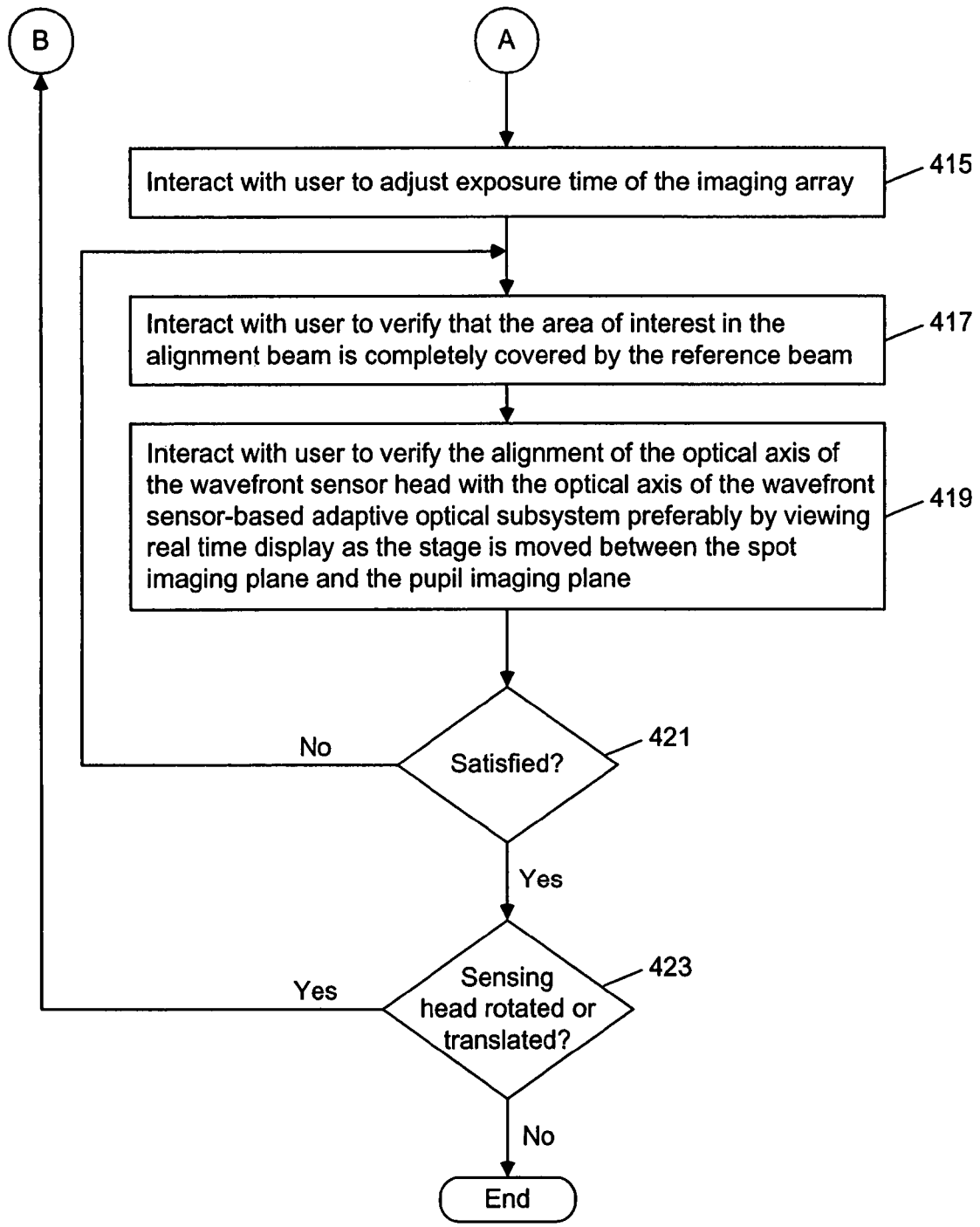

FIGS. 4A and 4B, taken together, illustrate an exemplary procedure for alignment of the Shack-Hartmann wavefront sensing head 303 of FIGS. 3A-(C). Notably, this alignment procedure is iterative in nature. Most users will continue to iteratively make smaller and smaller adjustments in a convergent procedure until everything is just right. The design of this alignment procedure allows for the iterative cycling between different alignment steps. The alignment procedure, which involves a graphical user interface (GUI) executing on the image processing and/or display apparatus 223, is presented herein in a manner that interactively guide a novice user automatically through all the steps of the alignment cycle. Ultimately, an experienced user will intuitively understand which alignment steps can be ignored and the order in which the steps should be executed to match the users particular iterative procedure. For this reason, the alignment procedure (and the associated graphical user interface) may be tailored to allow users to execute different alignment steps in any order.

It is assumed that prior to this alignment procedure, the following steps have been taken. First, the optical axis of the wavefront sensor head 303 has been roughly aligned with the optical axis the wavefront sensor-based adaptive optical subsystem 203 (which is aligned with the optical axis of the optical subsystem 201). Second, the relay lens 309 is positioned at the pupil image plane (i.e., the point where the plane of lenslet array 307 is imaged by the relay lens 309 onto the imaging device 311) and, the entire wavefront sensor head 303 is positioned so that the lenslet array 307 is conjugate to the system pupil (i.e., pupil of the subject eye). Third, an alignment beam (which is preferably produced by the optical subsystem 201 illuminating a model eye (e.g., mirror) and directing reflections of the model eye to the wavefront sensor-based adaptive optical subsystem 203) is directed along the optical axis of the wavefront sensor-based adaptive optical subsystem 203. Finally, the imaging processing and display apparatus 223 is in operable communication with the image storage processing and output device 310 of the sensor head 303 to generate a real-time display of the image data captured by the imaging device 311 of the sensor head 303.

In step 401, the graphical user interface (GUI) displays the real-time display and simultaneously the user interacts with the GUI to verify that this image has satisfactory characteristics (such as uniform illumination and expected shape).

In step 403, the user interacts with the GUI to adjust the exposure time of the imaging device 311 of the wavefront sensor head 303 (so that the image is neither saturated nor so dim as to be virtually invisible, when viewing the real-time display).

In step 405, the GUI displays the real-time display and the user interacts with the GUI to verify that the alignment beam is positioned so that it is centered on the lenslet array 307 and imaging device 311. If this is not the case, then the user may be instructed by the GUI to translate the wavefront sensor head 303 perpendicular to the alignment beam.

In step 407, the GUI displays the real-time display and the user interacts with the GUI to verify that the alignment beam is focused on the lenslet array 307 (and on the imaging device 311). If this is not the case, then the user may adjust the focus by adjusting focusing optics external to the wavefront sensor head 303 or moving the sensor head 303 linearly along the optical axis.

In step 409, the user interacts with the GUI to verify the alignment of the optical axis of the wavefront sensor head 303 with the optical axis the wavefront sensor-based adaptive optical subsystem 203 (which is aligned with the optical axis of the optical subsystem 201). This is preferably accomplished by displaying the real-time display while moving the moveable stage (e.g., relay lens 309 and imaging device 311) between the spot imaging plane and the pupil imaging plane. The spot imaging plane is the focal plane of the lenslets of the lenslet array 307 whereby the spot pattern formed therein is imaged by the relay lens 309 onto the imaging device 311. The pupil imaging plane, as described above, is the point where the plane of lenslet array 307 is imaged by the relay lens 309 onto the imaging device 311. As the stage nears the pupil image plane, the spots of the spot pattern spread and a "grid" formed by the fiducial points on the lenslet array 307 becomes evident. When the grid pattern is substantially aligned with the alignment spot pattern, alignment of the optical axis of the wavefront sensor head 303 with the optical axis the wavefront sensor-based adaptive optical subsystem 203 is satisfactory. Otherwise, the user is instructed to rotate (i.e., adjust the pitch and/or yaw) of the sensor head 303 until the grid pattern is substantially aligned with the spot pattern. It is important to realize that unless the alignment beam is very flat (phase-aligned), the alignment spot pattern will not lie directly behind their respective lenslets. It is only in the average sense that the user should try to eliminate misalignment between the grid pattern and the alignment spot pattern.

In step 411, the GUI provides the user the opportunity to repeat steps 405, 407 and 409 until the user is satisfied that these steps have been accomplished.

In step 413, the alignment beam is turned off, the reference source 315 is turned on, which produces the reference beam directed along the optical axis of the wavefront sensor 213', and the moveable stage (e.g., relay lens 309 and imaging device 311) is positioned such that relay lens 309 is positioned in the pupil imaging plane.

In step 415, the user interacts with the GUI to adjust the exposure time of the imaging device 311 of the wavefront sensor head 303 (so that the image is neither saturated nor so dim as to be virtually invisible, when viewing the real-time display).

In step 417, the user interacts with the GUI to verify that the area of interest in the alignment beam is completely covered by the reference beam. This preferably involves overlaying the image of the alignment beam recorded after the last execution of the alignment beam focusing operation (step 407) onto the real-time display of the reference beam.

In step 419, the user interacts with the GUI to verify the alignment of the optical axis of the wavefront sensor head 303 with the optical axis the wavefront sensor-based adaptive optical subsystem 203 (which is aligned with the optical axis of the optical subsystem 201). This is preferably accomplished by operations similar to those in step 409 with respect to the alignment beam. More specifically, the real-time display is displayed while moving the moveable stage (e.g., relay lens 309 and imaging device 311) between the spot imaging plane and the pupil imaging plane. The spot imaging plane is the focal plane of the lenslets of the lenslet array 307 whereby the spot pattern formed therein is imaged by the relay lens 309 onto the imaging device 311. The pupil imaging plane, as described above, is the point where the plane of lenslet array 307 is imaged by the relay lens 309 onto the imaging device 311. As the stage nears the pupil image plane, the spots of the spots of the reference spot pattern spread and a "grid" formed by the fiducial points on the lenslet array 307 becomes evident. When the grid pattern is substantially aligned with the reference spot pattern, alignment of the optical axis of the wavefront sensor head 303 with the optical axis the wavefront sensor-based adaptive optical subsystem 203 is satisfactory. Otherwise, the user is instructed to rotate (i.e., adjust the pitch and/or yaw) of the sensor head 303 until the grid pattern is substantially aligned with the reference spot pattern. It is important to realize that unless the reference beam is very flat (phase-aligned), the spot pattern will not lie directly behind their respective lenslets. It is only in the average sense that the user should try to eliminate misalignment between the grid pattern and the reference spot pattern.

In step 421, the graphical user interface provides the user the opportunity to repeat steps 417-419 until the user is satisfied that these steps have been accomplished.

Finally, in step 423, if the user has rotated or translated the sensing head 303, the graphical user interface provides the user the opportunity to repeat steps 401-421 until the user is satisfied that these steps have been accomplished.

Figure 5:
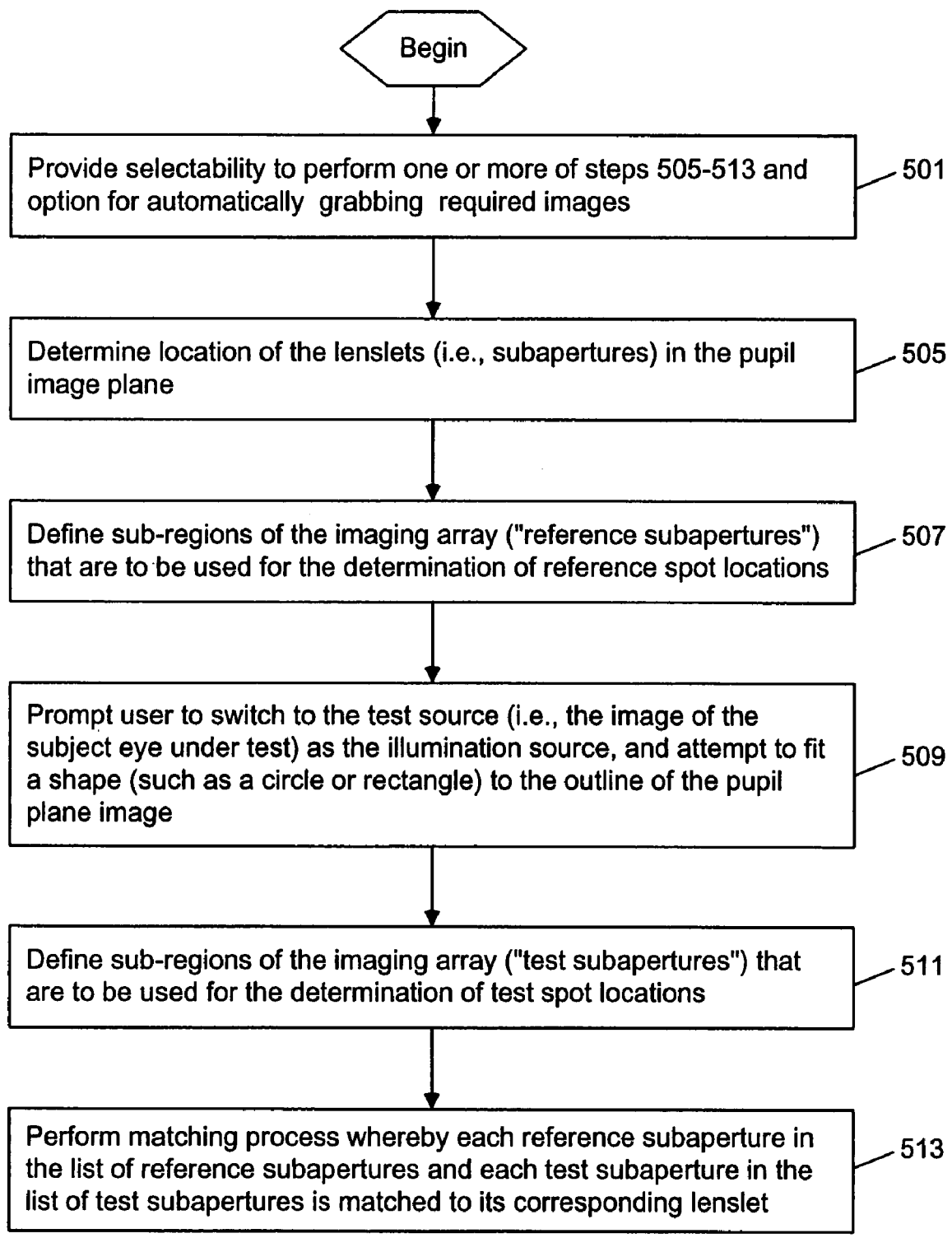
FIG. 5 is a flow chart illustrating exemplary operations for calibrating the Shack-Hartmann wavefront sensing components shown in FIGS. 3A-(C).

FIG. 5 illustrates an exemplary procedure for determining calibration parameters (including a dynamic mechanism that addresses the dot crossover problem) of the Shack-Hartmann wavefront sensing head 303 of FIGS. 3A-3C. The purpose of calibration of the Schack-Hartmann wavefront sensing head 303 is to determine the conversion factor between spot motion for a given lenslet and local wavefront tilt at the lenslet. This conversion factor is dependent upon the distance between the pupil image plane and the spot image plane and the radius of the pupil of the lenslet (and possibly the refractive index of the lenslet). A more detailed description of the construction for relating spot motion to local wavefront tilt is described in detail by Geary in "Introduction to Wavefront Sensors", SPIE Optical Engineering Press, 1995, pp. 14-20. The distance between the pupil image plane and the spot image plane focal length for a given lenslet is set by the distance that the moveable stage (e.g., the relay lens 309 and imaging device 311) moves from the pupil image plane to the spot imaging plane, and the radius of the pupil of the lenslet is set by the size of the individual lenslet elements. Since both of these quantities are determined at the time of manufacture, this basic calibration need not be re-measured each time the system is used.

There are, however, a number of parameters related to a particular wavefront measurement that must be determined before that particular wavefront measurement can be made. These include the position of the image of the system pupil (e.g., the image of the retina under test) in the local coordinate system of the wavefront sensing head 303, and the positions of the reference spots. In addition, it is preferable that the system employ a mechanism that can dynamically identify the sub-arrays (pixel areas) of the imaging device 311 that will be used for the determination of both reference spot positions and test spot positions for a particular wavefront measurement in a manner that addresses the dot crossover problem as discussed above.

The calibration procedure set forth below determines these calibration parameters (and includes a dynamic mechanism that addresses the dot crossover problem). This calibration procedure, which involves a graphical user interface executing on the image processing and/or display apparatus 223, is designed to be nearly automatic in the sense that very little user interaction is required unless the system detects the possibility of errors.

It is assumed that prior to this calibration procedure, the following steps have been taken. First, the optical axis of the wavefront sensor head 303 has been aligned with the optical axis the wavefront sensor-based adaptive optical subsystem 203 (which is aligned with the optical axis of the optical subsystem 201). This may be accomplished by following the alignment procedure described above with respect to FIGS. 4A and 4B. Second, the relay lens 309 is positioned at the pupil image plane (i.e., the point where the plane of lenslet array 307 is imaged by the relay lens 309 onto the imaging device 311) and the entire wavefront sensor head 303 is positioned so that the lenslet array 307 is conjugate to the system pupil (i.e., pupil of the subject eye). Finally, the image processing and display apparatus 223 is in operable communication with the image storage processing and output device 310 of the sensor head 303 to generate a real-time display of the image data captured by the imaging device 311 of the sensor head 303.

In step 501, the graphical user interfaces provides the user with ability to select to perform one or more of steps 505, 507, 509, 511, and 513 (the default selection is automatically perform steps 505, 507, 509, 511, and 513). In addition, the graphical user interface provides the user with the option of automatically grab the images required to perform the calibration operations in steps 505, 507, 509, 511, and 513 as described below. When this automatic grabbing option is activated, the graphical user interface may provide the user with a sub-option that allows the system to automate intensities of the grabbed images whereby the system checks exposure and make any corrections necessary. In addition, when this automatic grabbing option is activated, the graphical user interface may provide the user with a sub-option that allows the system to average reference positions whereby, instead of grabbing one image (default), the system grabs multiple images (such as 16), averages the pixel values of the multiple images, and saves the average pixel values for use in the calibration process.

In step 505, the system determines the location of the lenslets (i.e., subapertures) of the lenslet array 307 in the pupil image plane. Knowledge of the location of these subapertures in the pupil image plane is critical to accurate measurement of the shape of the wavefront. Preferably, the location of these subapertures is determined by grabbing slightly out-of-focus images of the lenslet array 307 obtained with the reference source as illumination. These images show the edges of the lenslets 307 as either bright or dark lines (depending on the sense of the defocus) against the uniform pupil background. The system uses Fourier transform techniques to fit a regular grid to these images, and tests the parameters of that grid against known parameters of the lenslet array 307 (for example, by testing whether the crosses of the grid lie at the centers of the lenslet array 307) to assure that there is no significant error in the fitting process. If an error is noted, the user is alerted. In addition, in step 505, the user may specify a general transformation of the subapertures (i.e., subaperture grid) via the user specifying a translation, magnification, and/or rotation. Unless there are very significant temperature changes or the sensor head 303 has been subjected to mechanical shock, these parameters are unlikely to change. Typically, this calibration step need only be done infrequently. Of course, it must be repeated if the lenslet array 307 is changed.

In step 507, the system defines the sub-regions (i.e., pixel areas) of the imaging device 311, which are denoted "reference subapertures" for the sake of description, that are to be used for the determination of reference spot locations. In this step, the system preferably grabs an image of the reference source spots and locates the rough position of all of the "useable" reference spots in this image. Preferably, a predetermined criterion (for example, based upon intensity values of pixels covered by a given reference spot) is used to distinguish between "useable" and "unuseable" reference spots and to filter out such "unuseable" reference spots. Sub-regions of the imaging device 311 around each useable reference spot are defined and stored in a list of reference subapertures. The sizes of these sub-regions are made as large as possible without overlapping. In addition, the system determines if a reasonable number of "useable" reference spots have been found based upon the known spacing of the lenslet array 307 and the size of the imaging device 311. If an unreasonably low number of "useable" reference spots have been found, an error is reported and the user is given an opportunity to examine the subapertures as defined to decide if there is truly a problem.

It is important to realize that the reference subapertures (defined in step 507) are wholly separate from the sub-regions of the imaging that will be used for the measurement of the test source (which will be defined in step 511). It is this use of separate lists of subapertures and subsequent matching process (step 513) that allows the wave front sensor 303 to effectively resolve potential dot crossover problems and thus achieve very large dynamic range that includes highly aberrated eyes.

In step 509 and 511, the user is prompted to switch to the test source (i.e., the image of the subject eye under test) as the illumination source for the wavefront sensor head 303.

In step 509, the system will attempt to fit a shape such as a circle or rectangle (which is preferably selected via user interaction with a menu or buttons listing such shapes) to the outline of the pupil plane image (which is based on retinal reflections from the subject eye under test). After fitting the shape, the system may bring up an image display on the image processing and/or display apparatus 223 with the best fit shape overlaid on the pupil plane image. The shape of the pupil outline is primarily used for the calculation of polynomial decompositions of the wavefront. For example, Zernike and Seidel polynomial decompositions are derived from a circular pupil, whereas Monomials, Hermites, Chebychev, and Legendre polynomial decompositions are derived from a rectangular pupil. However, selection of the pupil shape outline has no direct effect on the wavefront measurement itself. In cases where there is no well defined pupil, any convenient pupil may be selected.

In step 511, the system performs similar operations as those of step 507 to define the sub-regions (i.e., pixel areas) of the imaging device 311, which are denoted "test subapertures" for the sake of description, that are to be used for the determination of test spot locations. In this step, the moveable stage is positioned such that the relay lens 309 is located at the spot image plane (i.e., the focal plane of the lenslets of the lenslet array 307 whereby the spot pattern formed therein is imaged by the relay lens 309 onto the imaging device 311). Preferably, the system then grabs an image of the test source spots and locates the rough position of all of the "useable" test spots in this image. A predetermined criterion (for example, based upon intensity values of pixels covered by a given test spot) is used to distinguish between "useable" and "unuseable" test spots and to filter out such "unuseable test spots." Sub-regions of the imaging device 311 around each "useable" test spot are defined and stored in a list of test subapertures. The sizes of these sub-regions are made as large as possible without overlapping. In addition, the system determines if a reasonable number of "useable" test spots have been found based upon the known spacing of the lenslet array 307 and the size of the imaging device 311. If an unreasonably low number of "useable" test spots have been found, an error is reported and the user is given an opportunity to examine the test subapertures as defined to decide if there is truly a problem.

In step 511, the user may be given the option to process only those test spots that fall within the outline of the pupil shape defined in step 509.

In step 513, the final step of the calibration process is performed whereby each reference subaperture in the list of reference subapertures and each test subaperture in the list of test subapertures is matched to its corresponding lenslet (i.e., the particular lenslet that produced the spot from which the subaperture is derived).

The matching process of step 513 preferably is accomplished by grabbing one or more additional images of the reference spot pattern that are taken slightly away from best reference spot focus. In this image(s), the location of the spot in each subaperture differs from that found in the image at best reference spot focus. This difference is due to any deviation of the direction of propagation from the optical axis of the lenslet. The positions measured in the images may be used to project the rays from a given reference spot back to the plane of the lenslet array 307 to generate a list of crossing locations at this plane for each reference subaperture.

In addition, the same steps are performed on one or more additional images of the test spot pattern that are taken slightly away from best test spot focus. The result is a list of crossing locations at the plane of the lenslet array 307 for each test subaperture.

The system then processes the lists of crossing locations and the associated aperture lists to find unique reference aperture/test aperture pairs whose crossing points match within a prescribed tolerance. The system then verifies that the crossing points for the reference aperture/test aperture pairs correspond to the location of different lenslets in the lenslet array (as determined in step 505). The ultimate result of the matching process of step 513 is a list of lenslet centers each with an associated reference subaperture and test subaperture. Finally, this list of lenslet centers is tested to verify that most test subapertures have been properly matched to lenslet centers. If this test indicates a potential problem, the user is alerted. Otherwise, the calibration process is complete.

It should be noted that the calibration procedure may provide the user with the option to selectively activate (or deactivate) any one of the test apertures. This may be accomplished by displaying an image of the test apertures (represented by rectangles) overlaid on an image of the test spot pattern and enable the user to selectively activate (or deactivate) a given test aperture by any one of the test by clicking on the corresponding rectangle on the display. Any deactivated test apertures are removed from the list of test apertures. After such editing, the matching process of step 513 must be executed again.

It should also be noted that at intervals during the measurement, the reference source may be introduced and wavefront data taken. This allows for verification of calibration of the zero point of the wavefront sensing head 303.

It is important to realize that the reference subapertures (defined in step 507) are wholly separate from the test subapertures (defined in step 511). It is this use of separate lists of subapertures and the subsequent matching process (step 513) that allows the wave front sensor 303 to effectively resolve potential dot crossover problems and thus achieve very large dynamic range that includes the wavefront sensing of highly aberrated eyes.

Figure 7:
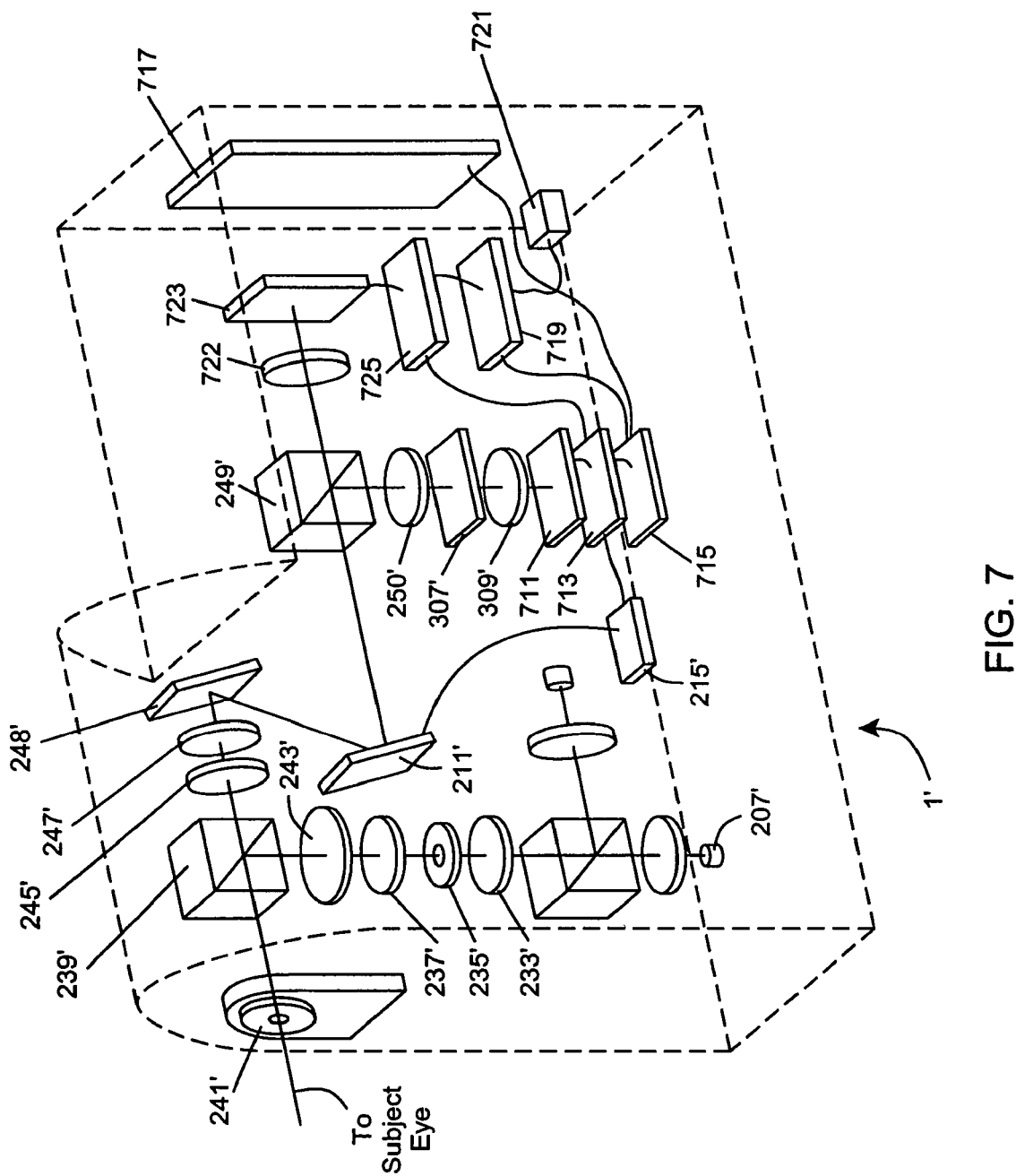
FIG. 7 is a schematic representation of an exemplary embodiment of a wavefront sensor-based ophthalmic imaging instrument (e.g., fundus camera) of the present invention.

Other inventive aspects of the fundus camera according to the present invention are shown in FIG. 7. More specifically, fundus camera 1' includes optical elements that image the light produced by imaging light source 207' onto the pupil of the subject eye, collect and collimate the light reflected from the retina of the subject eye, and direct such collimated light to a wavefront sensor-based subsystem. An exemplary embodiment of such optical elements includes a condenser lens 233', ring aperture 235', projection lens 237', diaphragm 243', first beam splitter 239' and objective lens 241' that image the light produced by the imaging light source 207' onto the pupil of the subject eye. Light reflected from the retina of the subject eye is collected and collimated by the objective lens 241', first beam splitter 239', focusing lens 245' and imaging lens 247'. Folding mirrors 248', second beam splitter 249' and relay lens 250' directs the collimated retinal reflections to recreate the distorted wavefronts (formed at the pupil of the subject eye) in the plane of a wavefront sensor (and possibly a deformable mirror 211' as shown).

As illustrated in FIG. 7, the wavefront sensor is preferably a Shack-Hartmann wavefront sensor including a lenslet array 307' and a moveable stage comprising a relay lens 309' and an imaging device. The lenslets of the lenslet array 307' partition the incident wavefront into a large number of smaller wavefronts, each of which is focused to a small spot on the imaging device. A more detailed description of the wavefront sensor is described above with respect to FIGS. 3A and 3B. The imaging device of the wavefront sensor preferably comprises an image sensor 711, image processor 713 and display interface 715 as shown.

The image sensor 711 captures images of the spot pattern and forwards image data representing these images to the image processor 713. The image processor 713 processes the image data provided thereto to track the spatial positions of these spots to derive the local slope (e.g., local gradients) of the incident wavefronts, which are used to reconstruct data representative of the aberrations of the distorted wavefronts (including defocus, spherical aberration, coma, astigmatism in addition to other higher order aberrations of the distorted wavefronts). For example, the image processor 713 may use the local gradients to reconstruct an optical path difference (OPD) array, which stores a scalar value that represents the optical path difference at each lenslet. Alternatively, the image processor 713 may use the local gradients to reconstruct an OPD function (for example by minimizing the difference between the derivatives of an analytical function—such as a set of Zernike polynomials, Seidel polynomials, Hermites polynomials, Chebychev polynomials, and Legendre polynomial- and the measured local gradients). Such reconstructed data represents the aberrations of the subject eye (including high order aberrations of the eye such as spherical aberration, astigmatism and coma).

The image processor 713 preferably operates as part of an adaptive optical feedback loop by supplying the data representative of the aberrations of the distorted wavefronts (such as the OPD array or OPD function) to the controller/driver 215', which controls the deformable mirror 211' to warp its optical surface to compensate for the phase aberrations measured by the wavefront sensor, thereby restoring the distorted wavefronts to phase-aligned wavefronts, which are directed to an imaging subsystem via beam splitter 249'.

In addition, the image processor 713 preferably generates data which graphically represents the aberrations of the subject eye (such as graphical icons representative of the reconstructed OPD function) and supplies such data to display interface 715, which operates to display such graphical representations on display device 717 (for example, a TFT LCD device) for view by the user. Such graphical representations provide the practitioner with valuable information characterizing the high order optical errors of the eye (which is far beyond the diopter information provided by current ophthalmic instruments) for use in diagnosis and treatment of abnormalities and disease in the eye.

Figure 11:
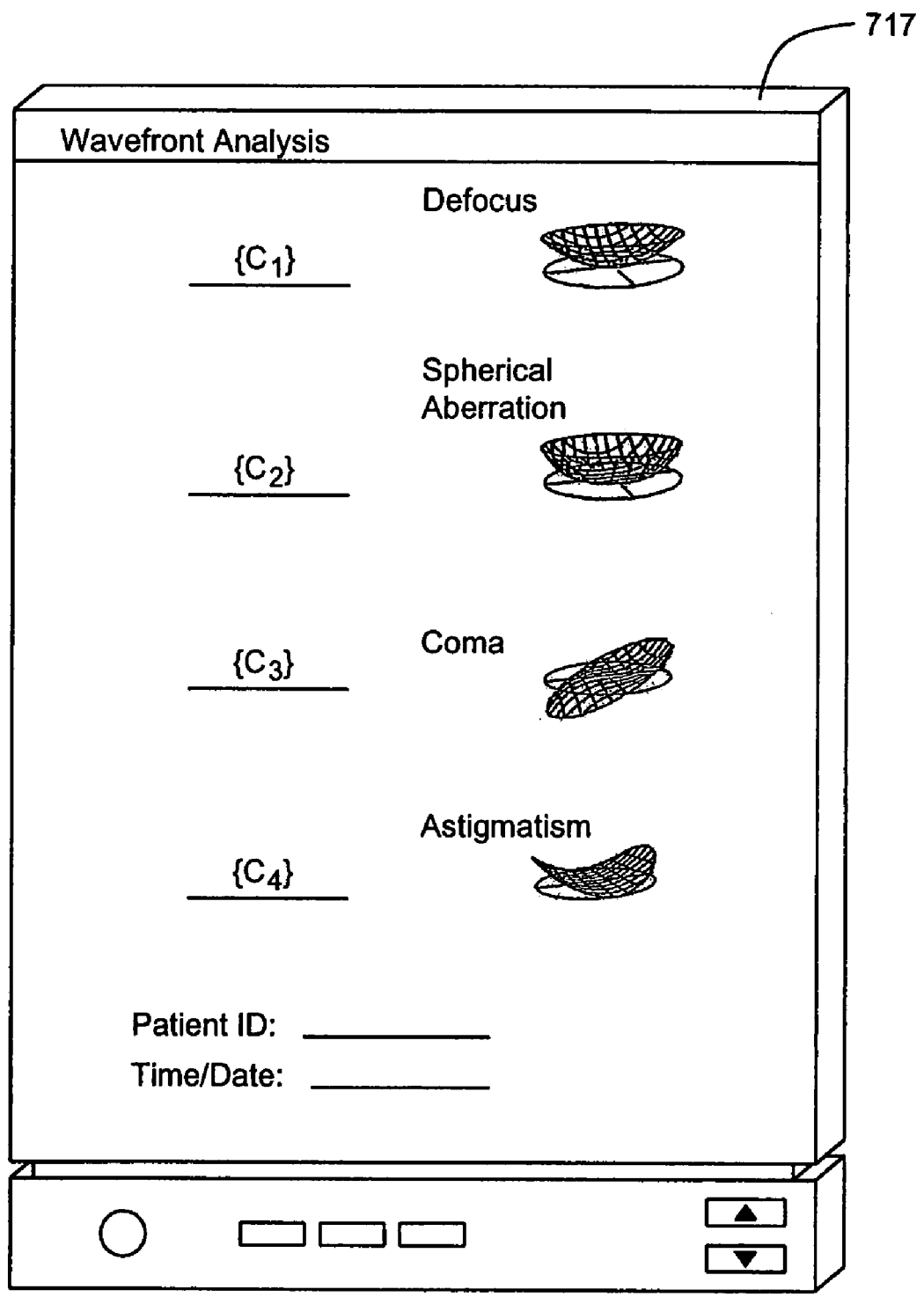
FIG. 11 is a schematic representation of a display viewable on the display device (in addition to a keypad) of the ophthalmic instrument shown in FIG. 7, wherein the display includes a graphical representation of the aberrations of the human eye (including high order aberrations of the human eye) as measured by the wavefront sensor of the ophthalmic instrument.

FIG. 11 illustrates an example of such graphical representations as displayed on the display device 717, which include two dimensional contour maps that graphically depict the contribution of pre-specified terms over the pupil of the wavefront sensor (e.g., for example terms of the OPD function such as defocus, spherical aberration, coma and astigmatism as shown) in the aberrations of the distorted wavefronts and corresponding coefficients (e.g., coefficients C1,C2,C3 and C4 of the terms of the OPD as shown) that define the maximum value these terms can have. The magnitude of these coefficients enables the practitioner to discern the relative strengths of the different terms (i.e., which term(s) dominate if any) and the two dimensional contour maps enable the practitioner to discern spatial variation of each term over the pupil of the wavefront sensor. Alternatively, the display device 717 may display predefined two-dimensional icons that provide a general graphical depiction of the pre-specified terms (e.g., defocus, spherical aberration, coma and astigmatism). Such icons provide the observer with a generalized view of the spatial variation of each term over the pupil of the wavefront sensor. In addition, the display includes the patient's identification information and the current time and date as shown. In addition, a touch pad 731 is shown, which includes keys that are used by the observer to control operation of the display device 717 and possibly other features of the camera 1'.

As shown in FIG. 7, the image processor 713 preferably interfaces to an I/O communication module 719 (such as a USB serial communication module) that provides communication to external devices (such as an external computer work station) over a communication link, for example via connector 721. The communication link can be used to communicate the image data processed by the image processor 713, the data representative of the aberrations of the subject eye (such as the OPD array or OPD function), and/or the data representing graphical icons of the aberrations of the subject eye (such as graphical icons representative of the OPD function) to the external devices for processing, analysis, display, printing, and/or archiving.

In addition, the fundus camera 1' includes an imaging subsystem including a relay lens 722 and an imaging device that capture images of the aligned wavefronts directed thereto by beam splitter 249' as shown in FIG. 7. The imaging device of the imaging subsystem preferably comprises an image sensor 723 and an image processor 725. The image sensor 725 captures images of the phase-aligned retinal reflections imaged therein and forwards image data representing these images to the image processor 725. The image processor 725 processes the image data provided thereto (for example, by compressing such image data). In addition, the image processor 725 preferably cooperates with the display interface 715 to display an image derived there from on display device 717. In addition, the image processor 725 preferably interfaces to the I/O communication module 719, which provides communication to external devices (such as an external computer work station) over a communication link, for example, via port connector 721. The communication link can be used to communicate the image data processed by the image processor 723 (or the raw image data provided thereto by the image sensor 723), which represents image(s) of the phase-aligned retinal reflections, to the external devices for processing, analysis, display, printing, and/or archiving.

It is also contemplated that the fundus camera 1' of FIG. 7 include a view finder (not shown) that is integrated into the optical path of the camera 1' to enable the user to view the reflections directed there through.

Figure 8A:
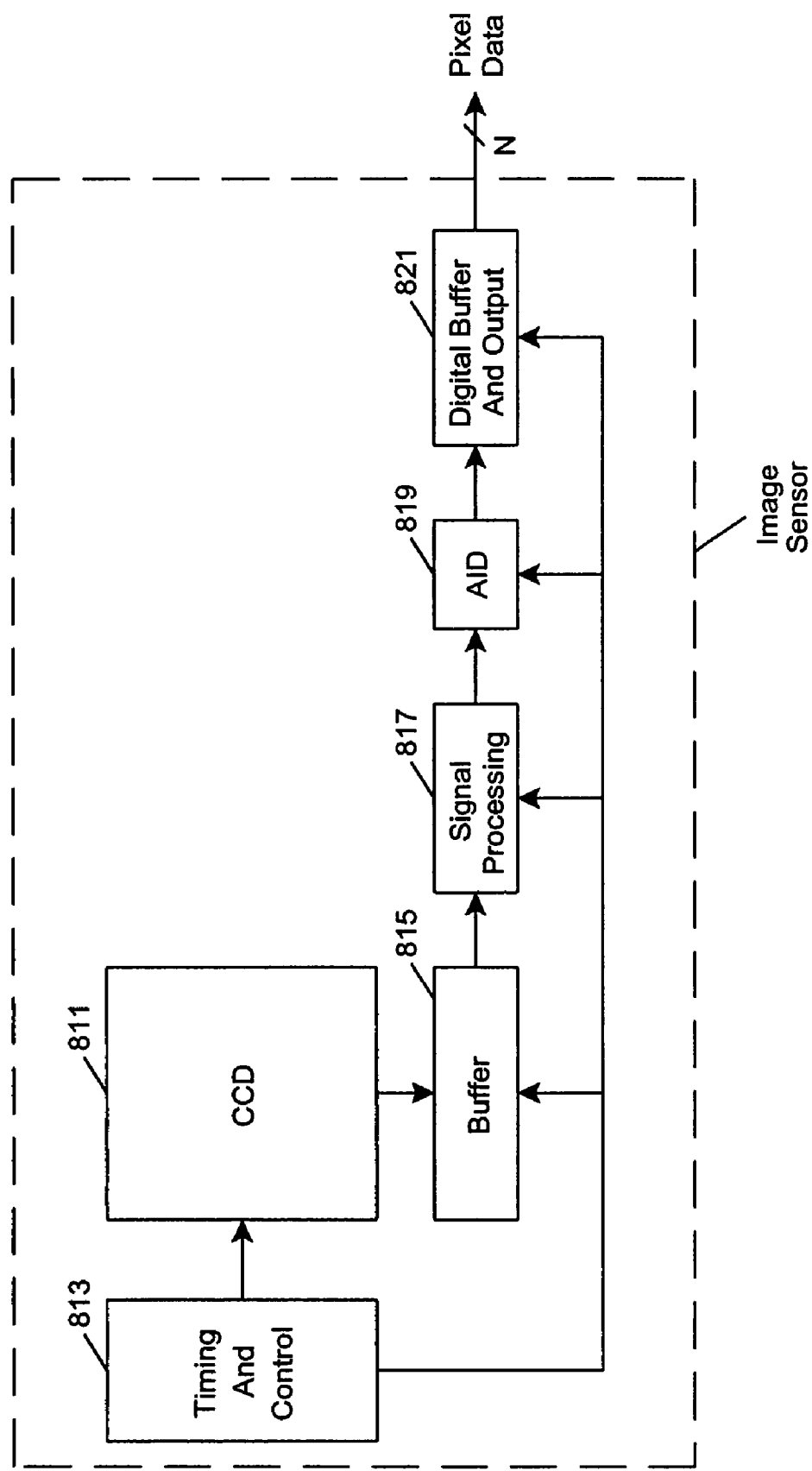
FIG. 8A illustrates an exemplary embodiment of the components of an image sensor, which may be used to embody image sensor 713 and/or image sensor 725 shown in FIG. 7.

FIG. 8A illustrates an exemplary embodiment of the components of an image sensor, which may be used to embody image sensor 713 and/or image sensor 725 of FIG. 7. The image sensor includes a CCD array 811 of photodetectors that detect the intensity of incident light thereon and generate an electrical signal in response thereto, timing and control circuitry 813 that supply timing signals to the CCD array 811 to: read out the electrical signals generated by the elements therein, store the signals in buffer 815, output the signals stored in buffer 815 to signal processing circuitry 817 that condition such signals for analogue-to-digital conversion circuitry 819, and store digital data words (pixel data words) derived from such signals in digital buffer and output circuitry 821 for output to image processing. Alternatively, a CMOS array or integrating CCD array may be substituted for the CCD array 811.

Figure 8B:
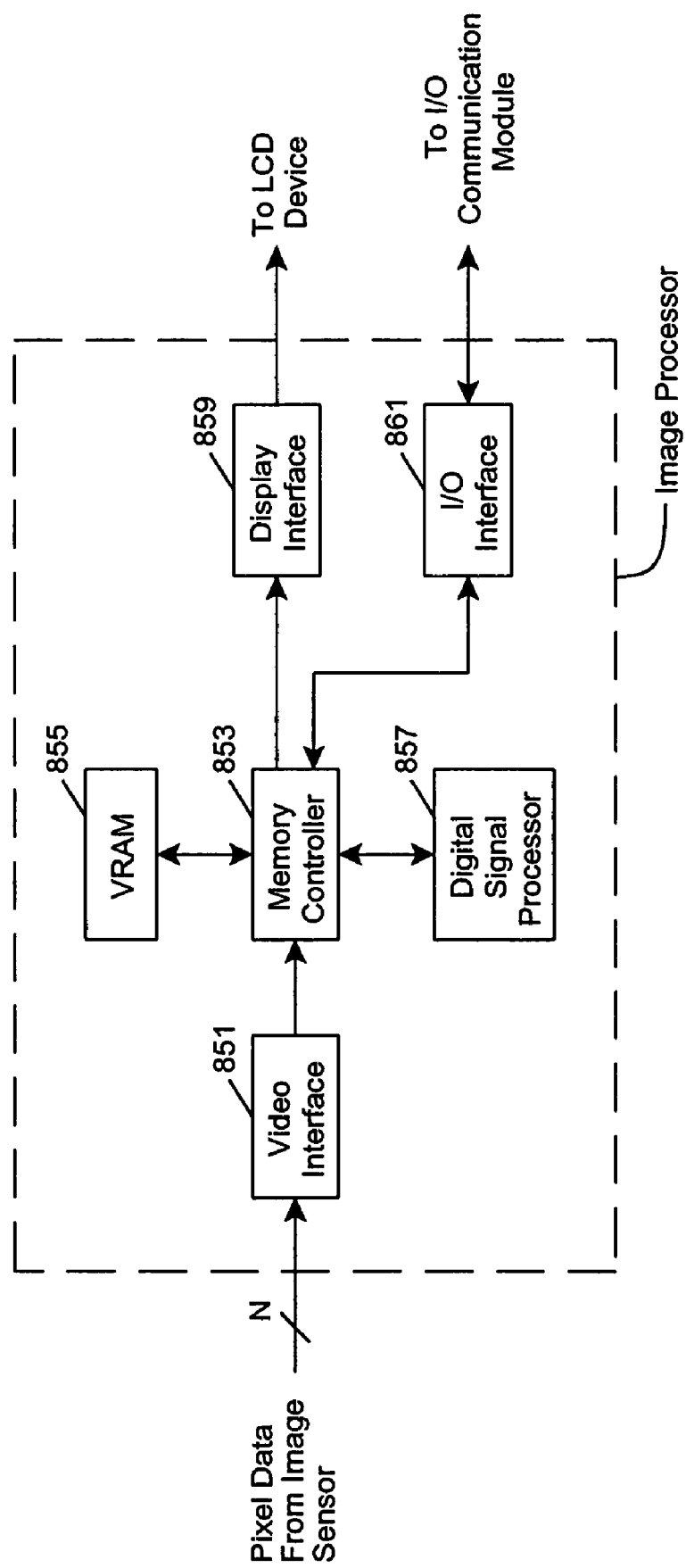
FIG. 8B illustrates an exemplary embodiment of an image processor, which may be used to embody image processor 713 and/or image processor 725 shown in FIG. 7.

FIG. 8B illustrates an exemplary embodiment of an image processor, which may be used to embody image processor 713 and/or image processor 725 of FIG. 7. The image processor includes a memory controller 853 that provides an interface to memory 855 for interface 851, digital signal processor 857, display interface 859 and I/O interface 861. Interface 851 inputs pixel data words from the image sensor and stores such pixel data words in memory 855 via memory controller 713. The digital signal processor 857 accesses the pixel data stored in memory 855 and processes such data in accordance with a sequence of programmed instructions. The display interface 859 provides an interface that supplies data for display on a display device (such as an TFT LCD device). Finally, I/O interface 861 provides a communications bus to external devices (such as the I/O communication module 719 of FIG. 7).

One skilled in the art will realize that the adaptive optical subsystem (e.g., wavefront sensor and deformable mirror—which operate to compensate for aberrations in the distorted wavefronts imaged thereon to form phase-aligned wavefronts), the imaging subsystem (which captures an image of the phase-aligned wavefronts formed by the adaptive optical subsystem) and possibly display interface and display (which operate to display the captured images on a display device) may be integrated into any ophthalmic imaging instrument that captures images of the eye, including corneal topographers, retinal topographers, corneal imaging devices, and retinal imaging devices.

In another aspect of the present invention, the wavefront sensor (e.g., lenslet array, image sensor and image processor), display interface and display device—which operate to generate and display graphical representations of the aberrations of the eye (including higher order aberrations such as spherical aberration, astigmatism and/or coma) are integrated into an ophthalmic instrument (for example, ophthalmic imaging instruments that captures images of the eye, including corneal topographers, retinal topographers, corneal imaging devices, and retinal imaging devices. In addition to ophthalmic examination instruments such as retinoscopes, autorefractors, slit lamps or other indirect opthalmoscopes).

Figure 9A:
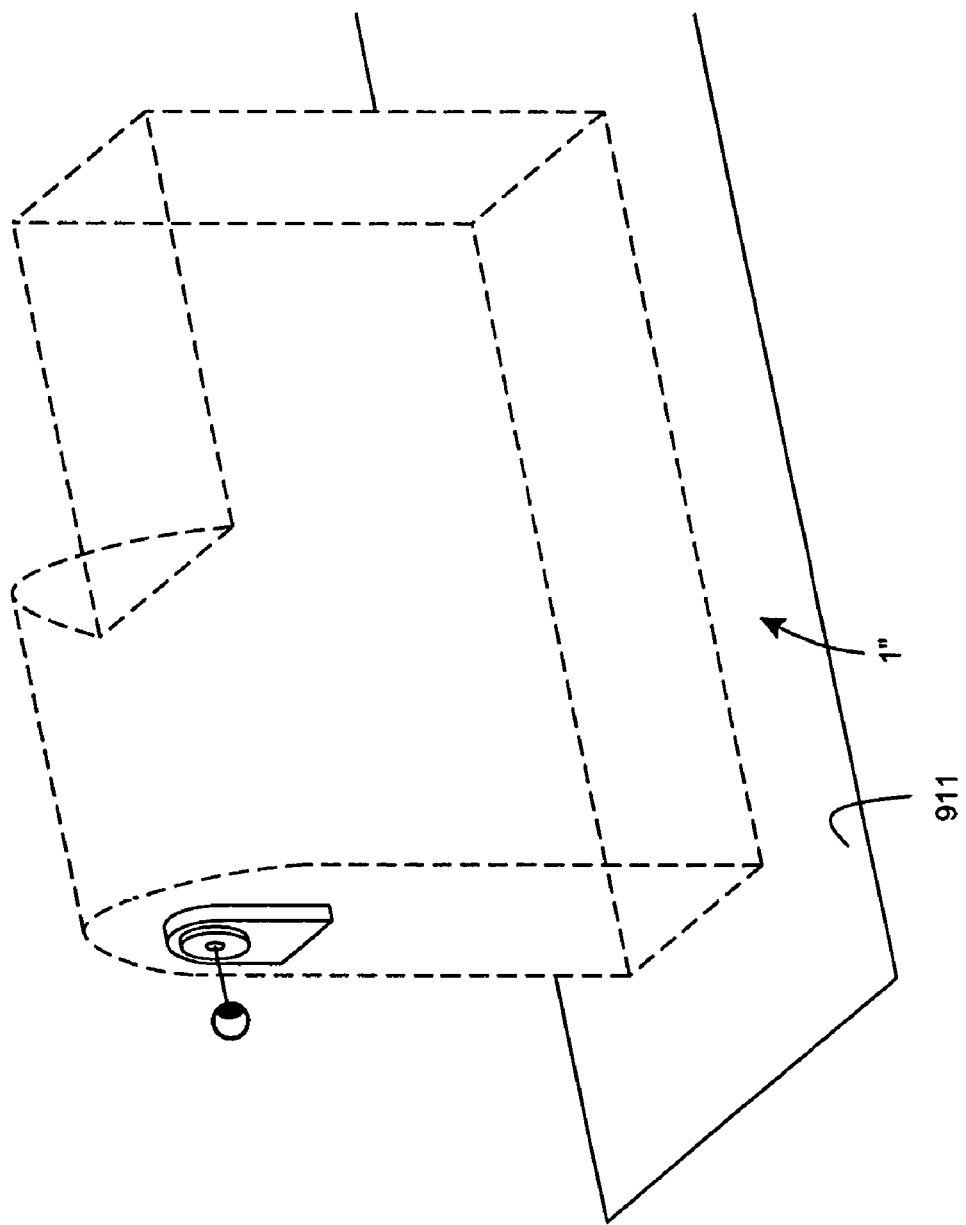
FIG. 9A is a schematic representation illustrating the configuration of the wavefront sensor-based ophthalmic instrument as a desktop instrument resting on a flat, stationary surface according to the present invention.
Figure 9C:
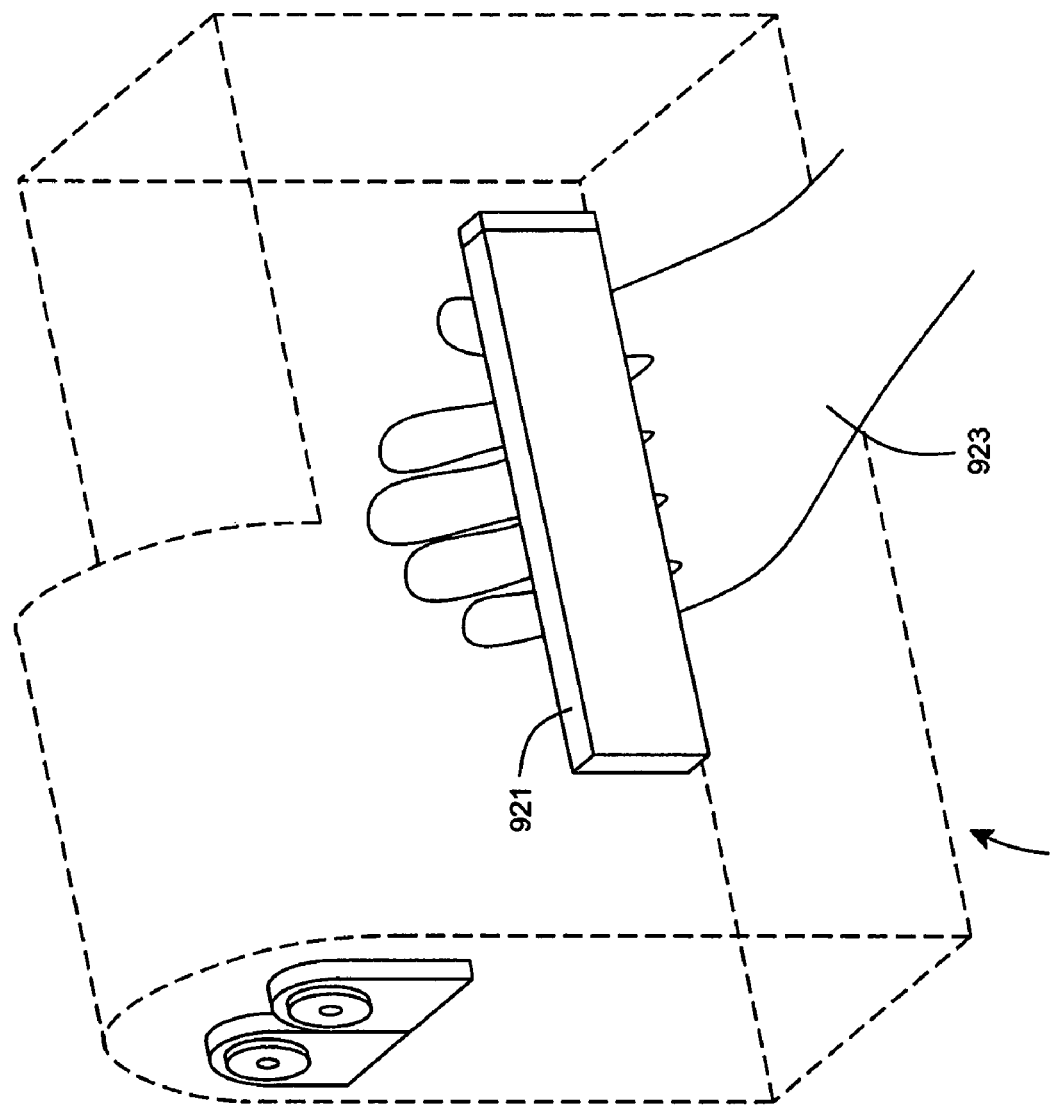
FIG. 9C is a schematic representation illustrating the configuration of the wavefront sensor-based ophthalmic instrument as a hand-held binocular instrument according to the present invention.

In yet another aspect of the present invention, a wavefront sensor-based ophthalmic instrument (for example, a fundus camera, retinoscope, autorefractor, slit lamp or other indirect opthalmoscope, corneal topographer, retinal topographer, corneal imaging device or retinal imaging device as described above) may be configured for different applications as illustrated in FIGS. 9A, 9B and 9C. In FIG. 9A, the wavefront sensor-based ophthalmic instrument 1″ is configured for use as a desktop instrument resting on a flat, stationary surface 911. In FIG. 9B, the wavefront sensor-based ophthalmic instrument 1‴ is configured for use as a hand-held instrument. In such a configuration, the wavefront sensor-based ophthalmic instrument 1‴ preferably includes a strap 921 affixed to the housing of the instrument that enables a user to comfortably hold the instrument by sliding hand 923 under the strap 921. In FIG. 9C, the wavefront sensor-based ophthalmic instrument 1″″ is configured as a hand-held binocular instrument. In this configuration, the optical train of the wavefront sensor-based ophthalmic instrument is duplicated (e.g., two channels, one for each eye). Any required image processing and control may be performed by separate devices for each channel (or such processing and control may be performed on one or more shared devices for the channels).

Figure 10A:
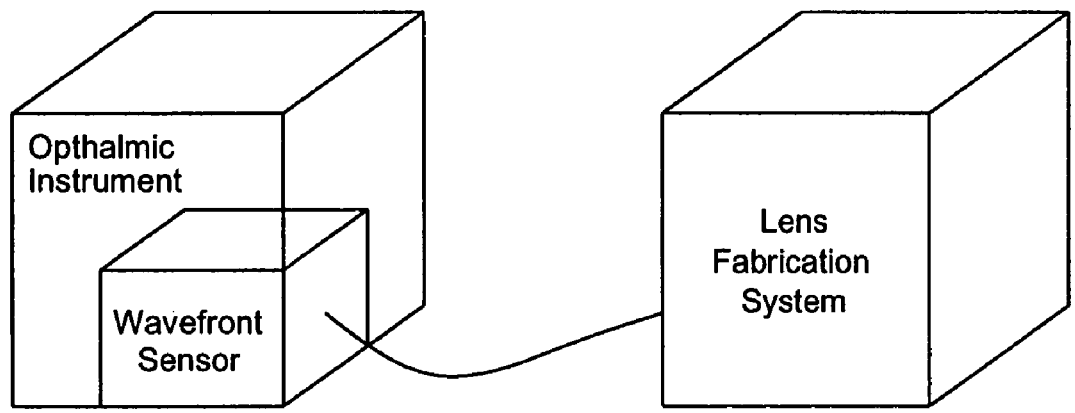
FIG. 10A is a schematic representation of a wavefront sensor-based ophthalmic instrument operably coupled to a lens fabrication system which fabricates lens (or contact lens or custom glasses), wherein the wavefront sensor of the instruments forwards data representative of the aberrations of the eye measured therein, such as the OPD array or OPD function (or data representative of the appropriate phase conjugated surface required to restore the aberrated wavefronts to phase-aligned reflected wavefronts), to the lens fabrication system.

In another aspect of the present invention, as illustrated in FIG. 10A, a wavefront sensor-based ophthalmic instrument (for example, a fundus camera, retinoscope, autorefractor, slit lamp or other indirect opthalmoscope, corneal topographer, retinal topographer, corneal imaging device or retinal imaging device as described above) forwards data representative of the aberrations of the eye measured therein, such as the OPD array or OPD function (or data representative of the appropriate phase conjugate surface required to restore the aberrated wavefronts to phase-aligned wavefronts), to a lens fabrication system which fabricates lens (or contact lens or custom glasses) that compensate for such aberrations. Examples of such lens fabrication systems are disclosed in U.S. Pat. Nos. 5,986,001; 5,789,461; 5,723,541; 5,158,717; and 6,086,204; each herein incorporated by reference in its entirety.

Figure 10B:
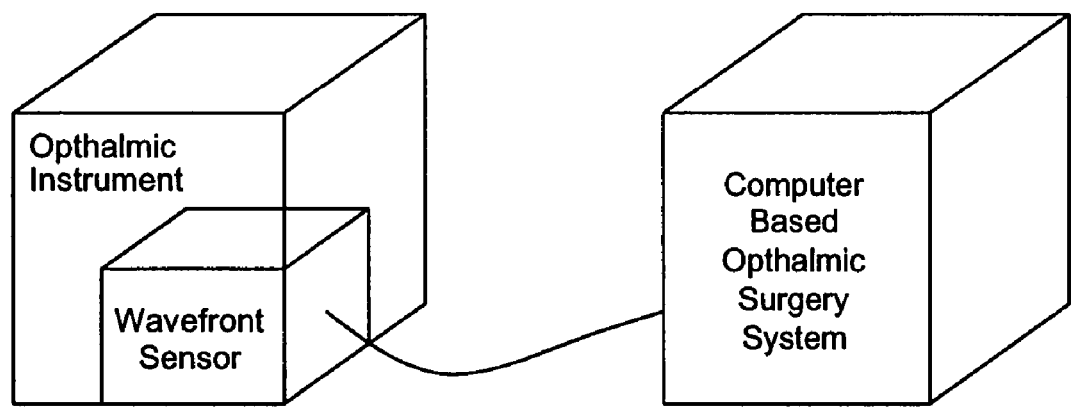
FIG. 10B is a schematic representation of a wavefront sensor-based ophthalmic instrument operably coupled to a computer-based ophthalmic surgery system (such as a laser refractive surgery system), wherein the wavefront sensor of the instruments forwards data representative of the aberrations of the eye measured therein, such as the OPD array or OPD function (or data representative of the appropriate phase conjugated surface required to restore the aberrated wavefronts to phase-aligned reflected wavefronts), to the computer-based ophthalmic surgery system such that it compensates for such aberrations when surgically treating the eye.

In yet another aspect of the present invention, as illustrated in FIG. 10B, a wavefront sensor-based ophthalmic instrument (for example, a fundus camera, retinoscope, autorefractor, slit lamp or other indirect opthalmoscope, corneal topographer, retinal topographer, corneal imaging device or retinal imaging device as described above) forwards data representative of the aberrations of the eye measured therein, such as the OPD array or OPD function (or data representative of the appropriate phase conjugate surface required to restore the aberrated wavefronts to phase-aligned reflected wavefronts), to a computer-based ophthalmic surgery system (such as a laser refractive surgery system) such that it compensates for such aberrations when surgically treating the human eye. Examples of such computer-based ophthalmic surgery systems are disclosed in U.S. Pat. Nos. 4,665,913; 4,669,466; 4,723,148; 4,770,172; 4,773,414; 4,665,913; 4,669,466; 4,729,372; 4,732,148; 4,770,172; 4,773,414; and 6,086,204; each herein incorporated by reference in its entirety.

In yet another aspect of the present invention, a wavefront sensor-based ophthalmic instrument (for example, a fundus camera, retinoscope, autorefractor, slit lamp or other indirect opthalmoscope, corneal topographer, retinal topographer, corneal imaging device or retinal imaging device as described above) forwards data representative of the aberrations of the eye measured therein, such as the OPD array or OPD function (or data representative of the appropriate phase conjugate surface required to restore the aberrated wavefronts to phase-aligned reflected wavefronts), to a practitioner to aid in the diagnosis and/or treatment of the eye.

Figure 12A:
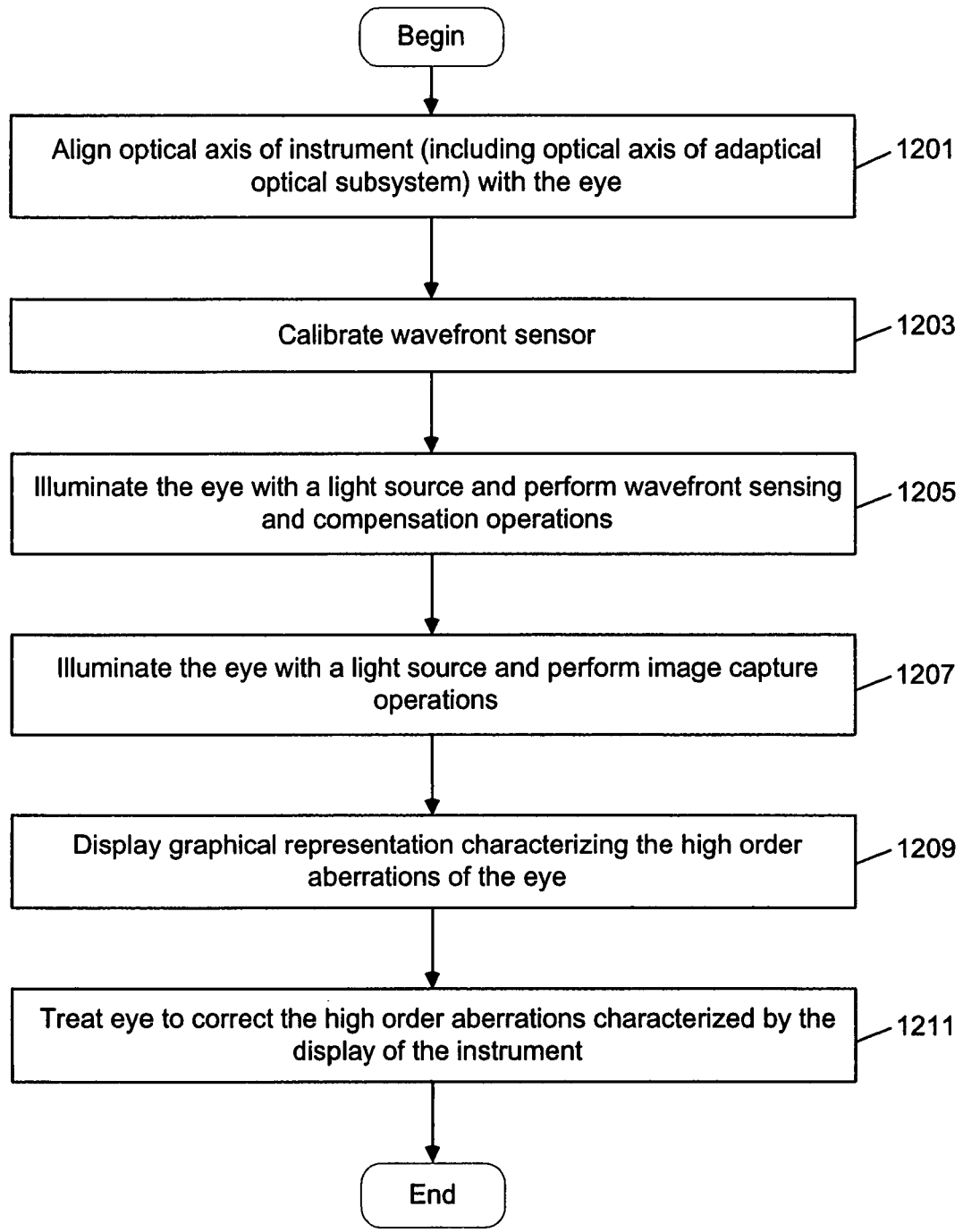
FIG. 12A is a flow chart illustrating operation of an adaptive-optics-based ophthalmic imaging instrument according to the present invention.

FIG. 12A illustrates operation of an adaptive-optics-based ophthalmic imaging instrument according to the present invention. In step 1201, the optical axis of the instrument (including the optical axis of the adaptive optical subsystem) is aligned with the eye. In a desktop instrument, this may be accomplished by aligning the eye to the optical axis of the desktop instrument, for example with the aid of a headband, chinrest, and fixation target (either external or internal) as described above. In a handheld instrument, this may be accomplished by aligning the optical axis of the instrument to the eye, for example with the aid of cross-hairs and infra-red distance detection as described above. In step 1203, the wavefront sensor is calibrated, if necessary. Exemplary calibration operations for the wavefront sensor of FIGS. 3A-3C is described above with respect to FIG. 5.

In step 1205, the eye is illuminated with light produced from a light source and wavefront sensing and compensation operations (as described above) are performed by the adaptive optical subsystem of the instrument. In step 1207, the eye is illuminated with light produced from a light source and image capture operations are performed by the imaging subsystem of the instrument thereby capturing an image (e.g., photograph or digital image captured by an image sensor) of the eye. The image may be an image of the retina or other portion of the ocular fundus, an image of the cornea, or an image of some other portion of the eye. Preferably, the wavefront sensing and compensation operations performed by the adaptive optical subsystem in step 1205 are performed concurrently with the image capture operation performed by the imaging subsystem in step 1207. In addition, in the preferred embodiment of the present invention as described above, the same imaging light source (e.g., flash lamp) is used as the illumination source when performing the wavefront sensing and compensation operations and the image capture operations.

In step 1209, the instrument preferably displays a graphical representation that characterizes the high order aberrations of the eye (as measured by the wavefront sensor).

Finally, in step 1211, the practitioner treats the eye (for example, by supplying a pre-fabricated contact lens or supplying a custom fabricated contact lens or surgical treatment) to correct the high order aberrations measured by the instrument. In addition, in step 1211, the practitioner can utilize the images captured by the instrument for diagnostic and pre-surgery purposes.

Figure 12B:
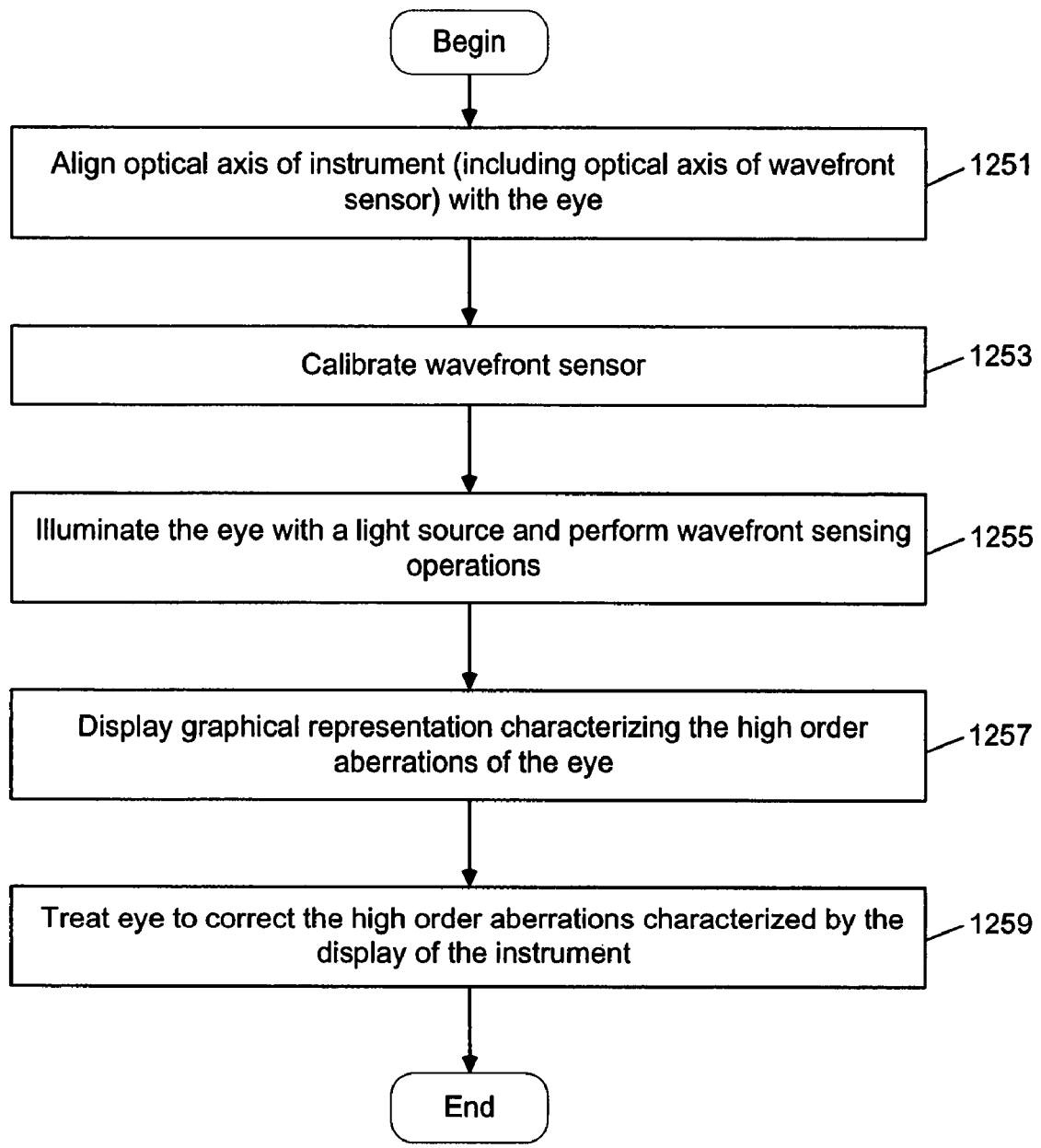
FIG. 12B is a flow chart illustrating operation of a wavefront sensor-based ophthalmic instrument according to the present invention.

FIG. 12B is a flow chart illustrating operation of a wavefront sensor-based ophthalmic instrument according to the present invention. In step 1251, the optical axis of the instrument (including the optical axis of the wavefront sensor) is aligned with the eye. In a desktop instrument, this may be accomplished by aligning the eye to the optical axis of the desktop instrument, for example with the aid of a headband, chinrest, and fixation target (either external or internal) as described above. In a handheld, instrument, this may be accomplished by aligning the optical axis of the instrument to eye, for example using a cross-hair and infra-red distance detection as described above. In step 1253, the wavefront sensor is calibrated, if necessary. Exemplary calibration operations for the wavefront sensor of FIG. 3A-3C is described above with respect to FIG. 5.

In step 1255, the eye is illuminated with light produced from a light source and wavefront sensing operations are performed by the wavefront sensor as described above.

In step 1257, the instrument displays a graphical representation that characterizes the high order aberrations of the eye (as measured by the wavefront sensor).

Finally, in step 1259, the practitioner treats the eye (for example, by supplying a pre-fabricated contact lens or supplying a custom fabricated contact lens or performing surgery) to correct the high order aberrations measured by the instrument.

SUMMARY AND ADVANTAGES OF THE PRESENT INVENTION

The ophthalmic imaging instrument of the present invention includes a wavefront sensor-based adaptive optical subsystem that measures phase aberrations (including higher order aberrations such as spherical aberration, coma, and/or astigmatism) in reflections derived from light produced by an imaging light source and compensates for such phase aberrations when capturing images of reflections derived from light produced by the same imaging light source.

The high-resolution image data captured by the ophthalmic imaging instrument of the present invention may be used to assist in detection and diagnosis of abnormalities and disease in the human eye and treatment (such as color imaging, fluorescein angiography, indocyanine green angiography) of abnormalities and disease in the human eye (including pre-surgery preparation and computer-assisted eye surgery such as laser refractive surgery) e.

Such high resolution image data (and pictures) reveal details of the structure of the retina that are not possible to obtain without the use of the wavefront sensor-based adaptive optical subsystem. Moreover, provided with such high-quality images (and pictures), practitioners can detect diseases earlier. For example, glaucoma damage can be detected only after prolonged destruction of the retina's nerve fiber layer. Such high quality images (and pictures) enable a practitioner to view details of the retina's nerve fiber layer for early detection of glaucoma. In addition, such high quality images (and pictures) enable practitioners to chart more precisely the retinal blood vessel damage resulting from diabetes and other diseases.

Advantageously, the ophthalmic imaging instrument of the present invention provides these benefits utilizing a single light source to perform the wavefront measurement and correction operations and imaging operations. Such a design significantly decreases the complexity and cost of the system. In addition, such a design is capable of executing in a continuous closed loop fashion whereby wavefront sensing and compensation is performed during imaging operations. Thus, the system can correct for aberrations (such as those due to blinking or accommodation) that occur after an initial wavefront sensing and compensation operations are complete (for example, during the subsequent imaging operations).

In addition, the ophthalmic imaging instrument of the present invention preferably includes an observation source that is used during an observation mode of operation to view (observe) the eye through a view finder, which expands the potential useful applications of the ophthalmic imaging instrument.

In addition, the ophthalmic imaging instrument of the present invention preferably includes a Schack-Hartmann wavefront sensor that includes a mechanism to resolve dot cross-over problems for highly aberrated eyes, thus providing an improved dynamic range of operation that enables measurement of an important class of eye aberrations.

In another aspect of the present invention, the optical subsystem, wavefront sensor-based optical subsystem and imaging subsystem of the ophthalmic imaging instrument (e.g., fundus camera) of the present invention are packaged in separate and distinct modular housings that interface via detachable connectors. In addition, the optical components of these modules are designed such that either the wavefront sensor-based adaptive optical subsystem or the imaging subsystem can be selectively interfaced directly to the optical subsystem (or directly to a relay lens adapter). Alternatively, the wavefront sensor-based optical subsystem and imaging subsystem may be packaged in a module housing separate and distinct from a module housing for the optical subsystem and interfaces thereto by detachable connectors. Such modular designs enables flexibility in meeting changing user demands.

In another aspect of the present invention, the wavefront-sensor based ophthalmic imaging instrument of the present invention can forward data that characterizes the high order aberrations of the eye as measured therein, such as the OPD array or OPD function (or data representative of the appropriate phase conjugated surface required to correct for such high order aberrations), to a lens fabrication system which fabricates lens (or contact lens or custom glasses) that correct for such aberrations. In addition, the wavefront sensor-based ophthalmic imaging instrument of the present invention can forward data that characterizes the high order aberrations of the eye as measured therein, such as the OPD array or OPD function (or data representative of the appropriate phase conjugated surface required to correct for such high order aberrations) to a computer-based ophthalmic surgery system (such as a laser refractive surgery system) such that it compensates for such aberrations when surgically treating the human eye.

In another aspect of the present invention, a method of treating the human eye includes the step of providing a wavefront sensor-based ophthalmic instrument that displays data that characterizes the high order aberrations of the eye as measured therein, such as the OPD array or OPD function (or data representative of the appropriate phase conjugated surface required to correct for such high order aberrations) to a practitioner for use in treating the eye. In addition, the wavefront sensor may be part of an adaptive optical subsystem that compensates for the phase aberrations measured therein to provide phase-aligned images of the eye for capture by an image capture subsystem. Such images may be used by practitioner in diagnosis and treatment of abnormalities and disease in the eye.

Other embodiments of the invention will be apparent to those skilled in the art from consideration of the specification and practice of the invention disclosed herein. It is intended that the specification and examples be considered as examples only, with the true scope of the invention being indicated by the Claims to Invention appended hereto.

What is claimed is:

1. A system for examining, diagnosing and treating abnormalities in the human eye, said system comprising:
   an ophthalmic imaging instrument having an integral adaptive optical subsystem disposed along the optical axis therein, and wherein the optical axis of the ophthalmic instrument is aligned with an eye of a patient;
   a light source for illuminating the eye with light produced from said light source and enabling said adaptive optical subsystem to perform wavefront sensing and compensation operations;
   wherein said wavefront sensing and compensation operations are performed by said adaptive optical subsystem, and a phase-aligned image of the eye is captured by an image capture system, for use by a practitioner in examining, diagnosing and treating abnormalities in the eye; and
   wherein a graphical representation of high order aberrations of the eye measured by said adaptive optical subsystem is displayed as two-dimensional contour maps that graphically depict contribution of pre-specified terms for aberrations of the eye.

2. The system of claim 1, wherein said phase-aligned image of the eye is a digital image captured by said image capture system.

3. The system of claim 2, wherein said graphical representation comprises coefficients corresponding to pre-specified terms that characterize aberrations of the eye.

4. The system of claim 2, wherein said pre-specified terms characterize defocus, spherical aberration, coma and astigmatism of said aberrations.

5. A system for examining, diagnosing and treating abnormalities in the human eye, said system comprising:
   an ophthalmic imaging instrument having an integral adaptive optical subsystem disposed along the optical axis therein, and wherein the optical axis of the ophthalmic instrument is aligned with an eye of a patient;
   a light source for illuminating the eye with light produced from said light source and enabling said adaptive optical subsystem to perform wavefront sensing and compensation operations;
   wherein said wavefront sensing and compensation operations are performed by said adaptive optical subsystem, and a phase-aligned image of the eye is captured by an image capture system, for use by a practitioner in examining, diagnosing and treating abnormalities in the eye; and
   wherein a graphical representation of high order aberrations of the eye measured by said adaptive optical subsystem is displayed as predefined two-dimensional icons that provide a general graphical depiction of pre-specified terms.

6. The system of claim 5, wherein said phase-aligned image of the eye is a digital image captured by said image capture system.

7. The system of claim 5, wherein said graphical representation comprises coefficients corresponding to pre-specified terms that characterize aberrations of the eye.

8. The system of claim 5, wherein said pre-specified terms characterize defocus, spherical aberration, coma and astigmatism of said aberrations.

* * * * *